(12) United States Patent
Thompson et al.

(10) Patent No.: US 7,457,765 B2
(45) Date of Patent: Nov. 25, 2008

(54) METHOD AND SYSTEM FOR SCHEDULING EMPLOYEES IN A PATIENT CARE ENVIRONMENT

(75) Inventors: Bruce J. Thompson, Morrison, CO (US); Glenda D. Graves, Arvada, CO (US); Delmur R. Mayhak, Jr., Arvada, CO (US)

(73) Assignee: Drason Consulting Services, LLC, Morrison, CO (US)

( * ) Notice: Subject to any disclaimer, the term of this patent is extended or adjusted under 35 U.S.C. 154(b) by 820 days.

(21) Appl. No.: 09/872,292

(22) Filed: Jun. 1, 2001

(65) Prior Publication Data

US 2001/0051888 A1      Dec. 13, 2001

Related U.S. Application Data

(60) Provisional application No. 60/209,107, filed on Jun. 2, 2000.

(51) Int. Cl.
*G06Q 90/00* (2006.01)
(52) U.S. Cl. .............................................. 705/9; 705/8
(58) Field of Classification Search ..................... 705/8, 705/9
See application file for complete search history.

(56) References Cited

U.S. PATENT DOCUMENTS

| | | | | |
|---|---|---|---|---|
| 4,937,743 A | * | 6/1990 | Rassman et al. ................ 705/8 |
| 5,065,315 A | | 11/1991 | Garcia ................... 364/413.01 |
| 5,111,391 A | | 5/1992 | Fields et al. ................. 364/401 |
| 5,732,401 A | | 3/1998 | Conway ........................ 705/29 |
| 5,748,907 A | | 5/1998 | Crane ......................... 395/202 |
| 5,809,477 A | | 9/1998 | Pollack ........................... 705/3 |
| 5,845,253 A | * | 12/1998 | Rensimer et al. ............... 705/2 |
| 5,913,201 A | | 6/1999 | Kocur et al. .................... 705/9 |
| 5,923,018 A | | 7/1999 | Kameda et al. ............. 235/385 |
| 5,924,074 A | | 7/1999 | Evans ............................. 705/3 |
| 5,970,466 A | * | 10/1999 | Detjen et al. ................... 705/8 |
| 5,991,728 A | | 11/1999 | DeBusk et al. ................. 705/2 |
| 5,995,937 A | * | 11/1999 | DeBusk et al. ................. 705/2 |

(Continued)

FOREIGN PATENT DOCUMENTS

WO      WO 97/25862      7/1997

(Continued)

OTHER PUBLICATIONS

Ho et al. Introducing variable-interval appointment scheduling rules in service systems, International Journal of Operations and Production Management, vol. 15, No. 6, 1995.*

(Continued)

*Primary Examiner*—Andre Boyce
(74) *Attorney, Agent, or Firm*—Merchant & Gould PC

(57) ABSTRACT

A system and method for managing a health clinic, and in particular to managing/scheduling employees to work in the clinic. The system and method relates to a computer program for computing the needs of patients, determining adequate staffing requirements and displays these needs and requirements in connection with actual scheduling values. Thus, the system provides a tool for quickly determining whether the clinic is overstaffed or understaffed, for the entire day based on patient needs, both direct and indirect patient care needs. The system and method may further use facility limitation information to provide overall efficiency information.

6 Claims, 23 Drawing Sheets

U.S. PATENT DOCUMENTS

| | | | |
|---|---|---|---|
| 6,044,355 A * | 3/2000 | Crockett et al. | 705/8 |
| 6,278,978 B1 * | 8/2001 | Andre et al. | 705/9 |
| 6,640,212 B1 * | 10/2003 | Rosse | 705/9 |
| 6,732,079 B1 * | 5/2004 | Kintner et al. | 705/8 |
| 6,823,315 B1 * | 11/2004 | Bucci et al. | 705/9 |
| 6,970,829 B1 * | 11/2005 | Leamon | 705/9 |
| 2002/0026342 A1 * | 2/2002 | Lane et al. | 705/8 |

FOREIGN PATENT DOCUMENTS

WO    WO 97/40463    10/1997

OTHER PUBLICATIONS

International Search Report for PCT/US01/17837.

* cited by examiner

| LAST NAME | FIRST NAME | EMPLOYEE ID | LOGIN ID | DOB | SCH_STATUS (DPC%) | JOB TYPE (DPC%) | ACTIVE/INACTIVE |
|---|---|---|---|---|---|---|---|
| ADMINISTRATOR | SAM | 111-11-1111 | SA1111 | 04/08/57 | AVAL ADM(0%) | E-AD(0%) | ACTIVE |
| NURSE | BOBBY | 111-11-1118 | BC1118 | 02/11/01 | AVAL DPC(100%) | CE-SO(13.75%) | ACTIVE |
| NURSE | DONNA | 111-11-1120 | DN1120 | 04/19/01 | TERM(0%) | A-ERNS(100%) | INACTIVE |
| NURSE | SHEILA | 111-11-1119 | SN1119 | 04/19/01 | XFER(0%) | CE-RNC(2.50%) | ACTIVE |
| NURSE | MARY | 111-11-1114 | MN1114 | 02/11/01 | AVAL DPC(100%) | CE-RNS(100%) | ACTIVE |
| NURSE | JILL | 111-11-1113 | JN1113 | 02/11/01 | AVAL DPC(100%) | CE-RNS(100%) | ACTIVE |
| NURSE | SUSAN | 111-11-1112 | SN1112 | 02/11/01 | AVAL DPC(100%) | CE-RNS(100%) | ACTIVE |
| REUSE | HERALD | 111-11-1122 | HR1122 | 04/27/01 | AVAL DPC(100%) | CE-RU(7.250%) | ACTIVE |
| TECH | DYLAN | 111-11-1123 | DT1123 | 04/19/01 | TRN(2.50%) | CE-PCT(100%) | ACTIVE |
| TECH | RANDY | 111-11-1121 | RT1121 | 04/14/01 | AVAL DPC(100%) | CE-T(27.50%) | ACTIVE |
| TECH | MARK | 111-11-1116 | MT1116 | 02/11/01 | AVAL DPC(100%) | CE-PCT(2.50%) | ACTIVE |
| TECH | BEN | 111-11-1115 | BT1115 | 02/11/01 | AVAL DPC(100%) | CE-PCT(100%) | ACTIVE |
| TECH | JOHN | 111-11-1117 | JT1117 | 02/11/01 | AVAL DPC(100%) | CE-PC(13.75%) | ACTIVE |

| HOURS PER TREATMENT REPORT | | ☒ |
|---|---|---|
| GENERAL | | |

SUMMARY
- REPORT DATE: 05/28/2001
- TOTAL TREATMENTS: 25
- PATIENT CARE HOURS WORKED: 29.38
- PATIENT CARE HPT: 1.18
- ADMINISTRATIVE HOURS WORKED: 17.63
- ADMINISTRATIVE HPT: 0.71
- TOTAL HPT: 1.88

ADJUSTMENTS TO HOURS WORKED ARE CALCULATED AS FOLLOWS: 1/2 HOUR LUNCH FOR EACH SHIFT OVER 4 1/2 HOURS LONG.

PRINT | CANCEL

METHOD AND SYSTEM FOR SCHEDULING EMPLOYEES IN A PATIENT CARE ENVIRONMENT

RELATED APPLICATION

This application claims the benefit under 35 U.S.C. §119 (e) of U.S. Provisional Application 60/209,107, entitled SCHEDULING SYSTEM, filed Jun. 2, 2000 by Bruce Thompson, which application is also hereby incorporated by reference in its entirety.

TECHNICAL FIELD

This invention relates generally to scheduling employees and more particularly to computer-aided systems for scheduling employees. More particularly, the present invention relates to computer-aided systems for scheduling employees in order to properly handle the many and various patient-care activities arising in a clinical environment especially wherein patients require a variable amount of employee attention during a visit to the clinic.

BACKGROUND OF THE INVENTION

In health care, given the importance of patient safety, maintaining an adequate staffing schedule is highly important to insure that the relative needs of the patients are satisfied. In order to adequately staff typical health-care locations, such as specialized clinics, several factors are typically considered. For instance, for a particular day, clinics typically determine the relative needs of each of the scheduled patients and schedule enough employees to handle these needs. The decision making is fairly individualized, such that for each patient, at least one employee is assigned the task of taking care of that patient's needs. These needs may be determined based on previous visits by a patient, especially in a clinic that provides regular, continual treatments to its patients, such as a dialysis clinic.

Additionally, clinics typically account for possible emergency situations and/or patients requiring additional treatment, i.e., treatment that was not scheduled. Since these events are not foreseeable but may occur, the clinics typically schedule some additional employees to handle these situations. When determining the number of employees to schedule, clinics therefore typically schedule employees based on a worst-case scenario to make sure that plenty of qualified employees work each day.

Unfortunately however, these worst-case scenarios do not happen regularly, such that many clinics are generally overstaffed, which reduces the efficiency of the clinic. Additionally, clinics often schedule many patient activities to occur at approximately the same time of the day such that many if not all the employees are busy during that time but are then idle for the remaining time, or until the next intermittent peak of activities occurs. Consequently, due to the lack of worst-case scenarios and unfortunate timing of patient activities, typical clinics are overstaffed and not as efficient as they might be.

It is with respect to these and other considerations that the present invention has been made.

SUMMARY OF THE INVENTION

The present invention relates to a system and method for managing a health clinic, and in particular to managing/scheduling employees to work in the clinic. In a particular embodiment of the invention, the system and method relates to a computer program for computing the needs of patients, determining adequate staffing requirements and displays these needs and requirements in connection with actual scheduling values. Thus, the system provides a tool for quickly determining whether the clinic is overstaffed or understaffed, for the entire day based on patient care needs.

In a particular embodiment, the scheduling method and system is used in a clinic that performs dialysis on patients and has a specific number of chairs or machines that can be used to perform the dialysis. The limitation of resources necessarily limits the number of patients that can be serviced at any time in the day. For this reason, the invention is helpful to schedule these patients in relation to the actual machines or chairs. Additionally, dialysis patients typically require differing amounts of care by licensed nurses or other capable, technical employees of the clinic. This added variable increases the difficulty in trying to staff a clinic in the most efficient manner, i.e., so that there are not too many or too few employees scheduled on a daily basis based on employee skill requirements for that day.

In accordance with certain aspects, the present invention relates to a system and method of scheduling a plurality of patients and a plurality of employees in a health care environment, wherein at least two patients receive treatment during a predetermined time period. Patient care requirements are evaluated for each patient, wherein the patient care requirements relate to actual employee time necessary to satisfy the patient care requirements. Also, in response to the patient care requirement evaluation, the scheduled time of at least one patient is adjusted in order to distribute the associated employee time requirements throughout a predetermined time period, such as a day. Additionally, employees are scheduled in response to the distributed employee time requirements.

In accordance with other aspects, the inventive method further relates to dividing the day into intervals and, in evaluating the patient care requirements, determining the patient care requirements on a per-interval basis. The patient care requirements may then be averaged over more than one interval. In another embodiment, a plurality of job types are predetermined, each job type having a different patient care capability value associated with each job type and wherein the method further relates to scheduling shifts of employees based on job type and then scheduling employees based on scheduled job type.

In accordance with other aspects, the present invention relates to a method of scheduling employees wherein the patient care capability value of each employee is averaged over an entire shift. The method further involves displaying a plurality of patient schedules in relation to time to provide a visual indication of the patient care requirements for each interval. The method may further calculate patient requirement values related to required employee based on the patient care requirements for a plurality of intervals and display the calculated values. These values may further be displayed along with employee shift information to provide a visual indication of scheduled is employee information in relation to scheduled patient information. Moreover, the values may be compared, as between the patient requirement values and employee values, for each interval to determine efficiency.

In accordance with yet other aspects, an embodiment of the invention schedules employees in a health care environment by compiling a plurality of patient profiles, each profile associated with a different patient, and wherein each profile comprises information related to the direct patient care needs of the associated patient; compiling a plurality of employee profiles, each profile associated with a different employee and wherein each profile comprises information related to the patient care capability of the associated employee; calculating efficiency information relating to a generated schedule of patients and employees based on the patient profiles and employee profiles; and adjusting the schedule to generate a more efficient schedule. In another embodiment, a system that schedules the employees has a memory store for storing patient information related to the needs of a plurality of patients, resource information and employee information related to patient care capability of a plurality of patients; a scheduling module that schedules patients and employees according to patient needs; and a display unit for displaying the scheduled patient information in combination with scheduled employee information, the display providing efficiency information, such as in a graphical user interface.

The invention may be implemented as a computer process, a computing system or as an article of manufacture such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

A more complete appreciation of the present invention and its improvements can be obtained by reference to the accompanying drawings, which are briefly summarized below, to the following detail description of presently preferred embodiments of the invention, and to the appended claims.

BRIEF DESCRIPTION OF THE DRAWINGS

FIG. 6 is a screen shot diagram illustrating the graphical display of the management system shown in FIG. 1, the display having a patient scheduling portion, an employee scheduling portion and calculation display region according to an embodiment of the present invention.

FIG. 7 is a screen shot diagram illustrating of the display shown in FIG. 6 populated with sample scheduling data according to an embodiment of the present invention.

FIG. 8 is a screenshot diagram illustrating a pop-up menu for editing a data related to a patient according to an embodiment of the present invention.

FIG. 10 is a screenshot diagram illustrating a pop-up menu for editing a data related to an employee or employee job type according to an embodiment of the present invention.

Figure 11:
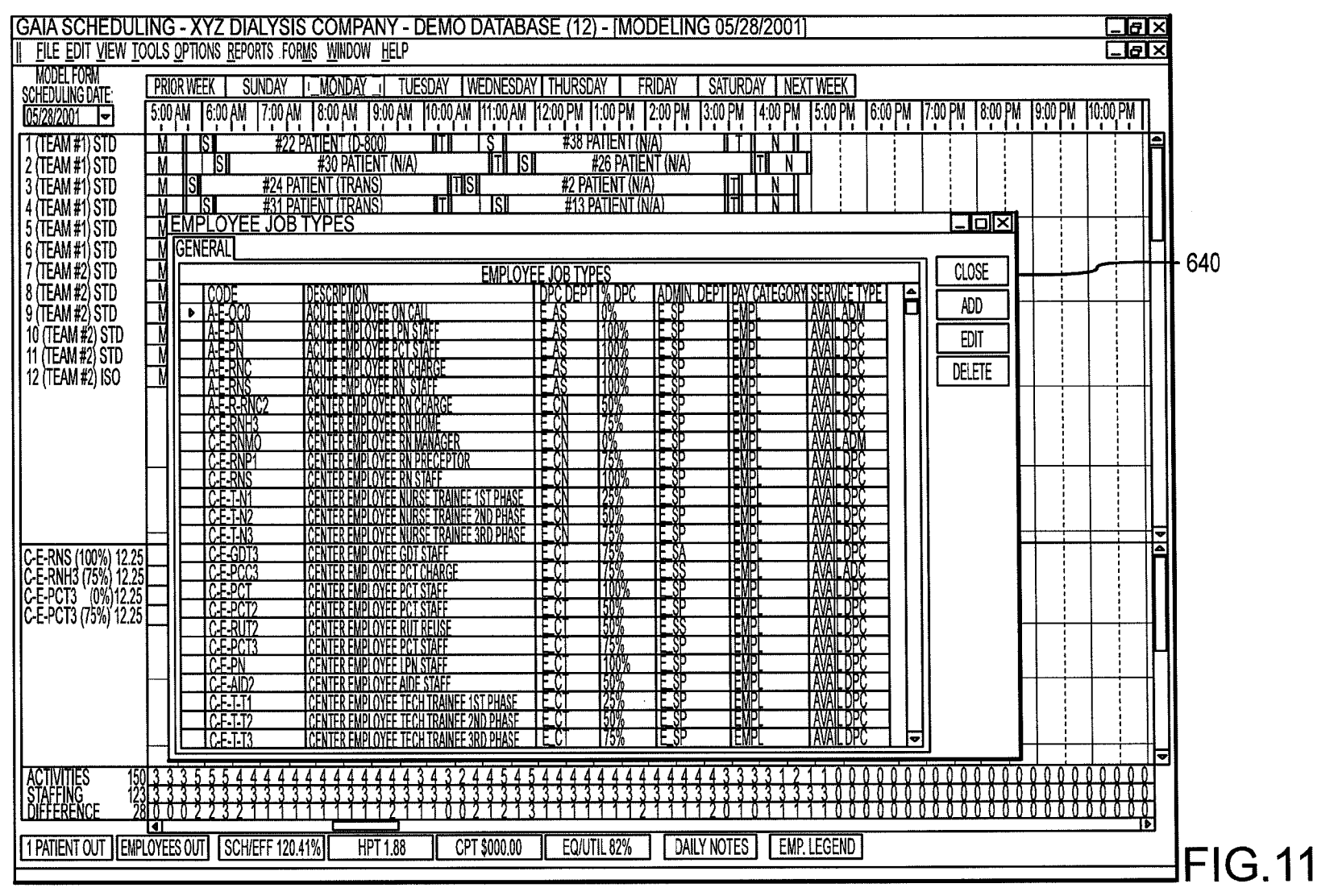

FIG. 11 is a screen shot diagram of an employee job-type window for entering or editing information related to job-types according to an embodiment of the present invention.

Figure 12:
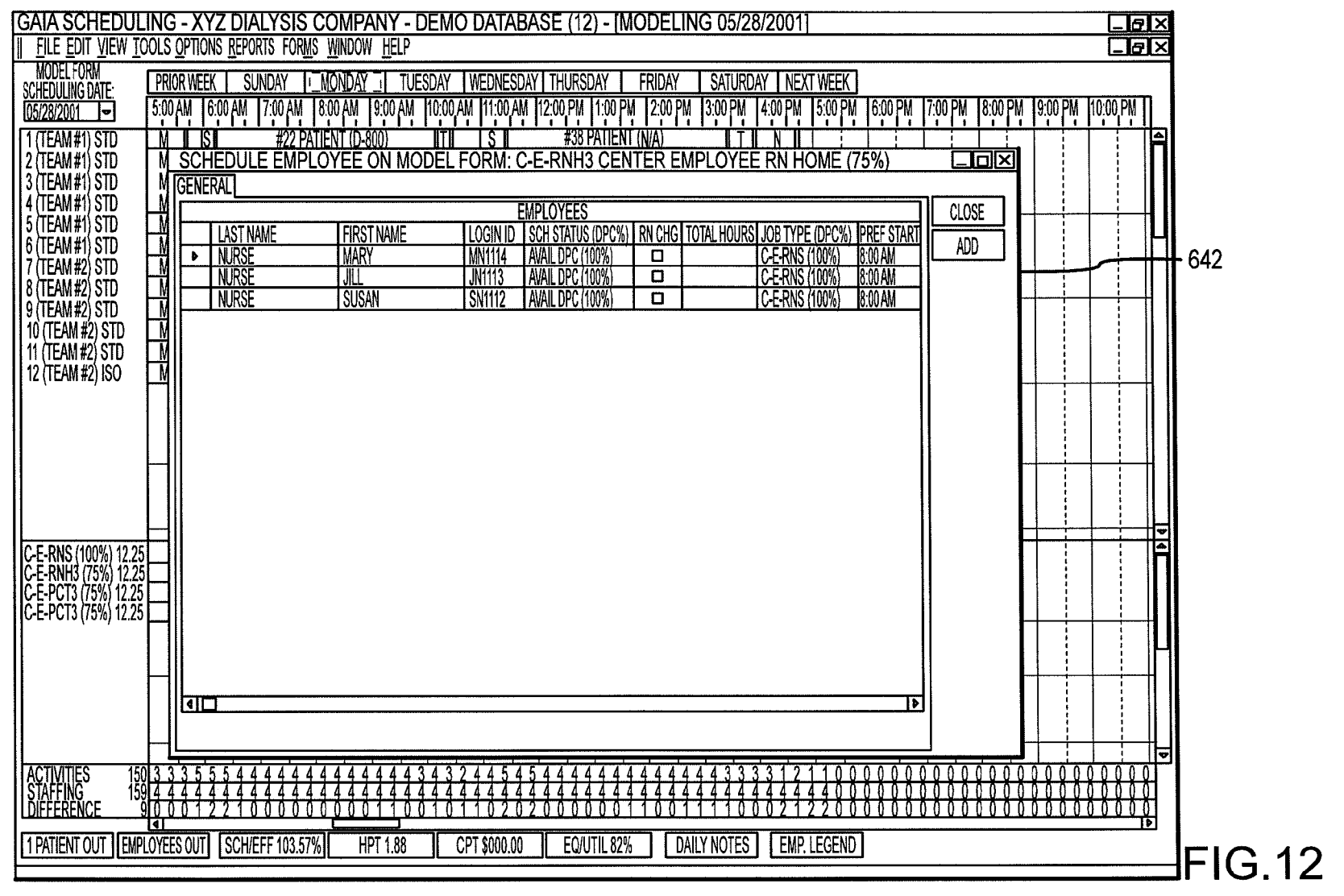

FIG. 12 is a screen shot diagram a pop-up window for scheduling an employee according to an embodiment of the present invention.

FIG. 13 is a screenshot diagram illustrating a pop-up, cascading menu for editing shift activities for a shift according to an embodiment of the present invention.

FIG. 15 is a screenshot diagram illustrating a information box according to an embodiment of the present invention.

FIG. 16 is a screenshot diagram illustrating a pull-down menu of viewable and editable lists according to an embodiment of the present invention.

FIGS. 17 and 18 are a screenshot diagrams illustrating viewable and editable lists according to an embodiment of the present invention.

FIGS. 19, 20 and 21 are a screenshot diagrams different pull-down menus according to an embodiment of the present invention.

FIGS. 22 and 23 are a screenshot diagrams different viewable records according to an embodiment of the present invention.

DETAILED DESCRIPTION OF THE INVENTION

Figure 1:
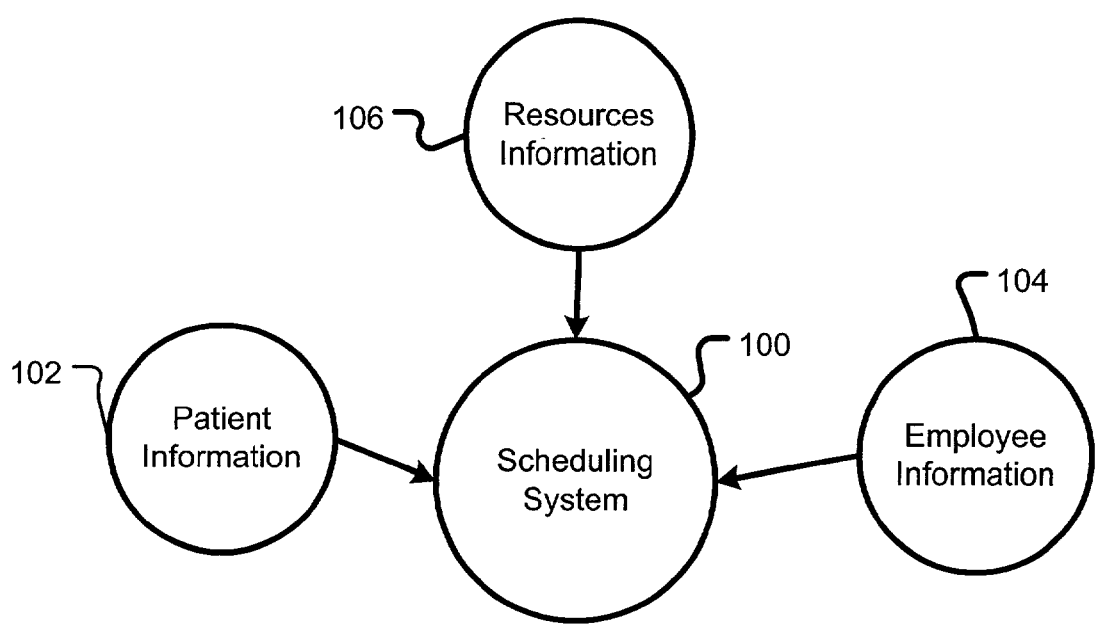
FIG. 1 is a diagram illustrating patient information and employee information in relation to a system for managing that information in accordance with aspects of the present invention.

A scheduling system 100 incorporating aspects of the present invention is shown in FIG. 1. The scheduling system 100 provides an automated system of creating a comprehensive schedule, taking into accounts the various needs and limitations of patients or "patient requirements," employees and available resources and displays all the necessary information for a user to quickly and readily identify inefficiencies in the schedule. The system 100 also provides an archival system for past and future services and report generating capabilities relating to efficiency calculations.

In an embodiment, the system 100 maintains various schedules for a "health service provider." As used herein, a "health service provider" provides predetermined health services and has the resources to do so, the resources relating to the employees, machines, and other items needed to accommodate various needs of patients. Particular health services may involves dialysis treatments or some other specialized health care treatment provided to patients on a relatively regular basis and wherein the treatment requires some amount of direct patient care administered by an employee of the health service provider. Although discussed herein with respect to dialysis treatments in a dialysis clinic, the present invention may be used to schedule requirements and employees in many other situations wherein employees have numerous and varied tasks and wherein the actual time needed to complete the tasks may be averaged over the course of an employee's shift.

The system 100 stores and uses patient information 102 which relates to specific patient needs and limitations and the types of services that are to be provided to the patient by the health service provider. For instance the patient information may relate to the number of hours needed to complete a visit and the types or amount of patient care, whether direct or indirect, that will be needed during each step in the delivery of care for each visit. The information may further include other requirements, e.g., limitations or restrictions relating to specific health conditions, etc. These requirements may affect the amount of direct patient care or indirect patient care that should be provided to the patient during a visit.

As used herein, the term "direct patient care," relates to direct attention paid to a patient such that the employee cannot handle any other task during the time the employee is providing direct patient care. Typically, the amount of direct patient care required by a patient can be predetermined based on past visits. That is, since many patients typically visit specialized clinics on a repeated, continual and regular basis, data may be collected relating to a patient's direct patient care needs. For example a patient may require approximately one and one-half hours of direct patient care during a four-hour visit, including initiating the dialysis treatment, administering the treatment, checking the machine or handling other more immediate tasks. Importantly however, a portion of the predetermined direct patient care relates to tasks that can be performed at different times, and are not necessarily performed at a specific time within the scheduled appointment.

The system 100 also stores information 104 related to the physical resources available. These types of resources may relate to reusable resources that may be allocated to a predetermined number of patients of at a particular time. For example, the physical resources may relate to rooms, dialysis chairs or machines, etc. that may allocated to a single patient at a time. Moreover, the system 100 may also store information related to the specific scheduling issues for the physical resources. As an example, a dialysis machine may not be allocated for patient care at all times, as the machine must be cleaned or otherwise disinfected between uses and the machine may need to be set up or otherwise configured for the next patient, such configuration may take a significant amount of time and the system 100 may plan for these particular requirements.

System 100 also stores and uses employee information 106 which has employee profile information. The employee profile information relates to employee scheduling requirements as well as employee capabilities. For instance, some employees may only be able to provide direct patient care on a limited basis, either because of other required duties or because of some other limitation, e.g., the employee is not fully trained or licensed for certain tasks. Additionally, the employee profile may indicate what job-type that person is qualified to perform.

In an embodiment of the invention, the employee information 106 includes model job types, such as a model for a certified nurse, a non-certified nurse, a technician, etc. These job types have certain, predetermined properties, such as whether the job type provides for direct patient care, and how much, as discussed below. In another embodiment the information 106 has other information related to shift activity. Shift activity information is provided to temporarily change the activity assigned to an employee, which may potentially change the amount of direct patient care that employee may perform during that shift. The information 106 may further relate to other activities such as indirect patient care, such as maintaining facility resources, etc. that a clinic may want to monitor in order to determine overall staffing and scheduling efficiency.

The system 100 uses the information 102, 104 and 106 to provide a resulting schedule of patient visits and employee shifts. The schedule is a daily schedule but could be set up on another basis. The daily schedule is divided into intervals, such as fifteen-minute intervals and displays values related the patient needs and/or the number of employees required to satisfy those needs on a per-interval basis. In an embodiment, the system displays each patient schedule portion with associated patient care tasks to provide a quick reference as to the needs of each patient with respect to the needs of the other patients with respect to the time of day. Thus, the patients' needs may be quickly viewed as creating a peak or inefficiency period. The system may also provide a means of adjusting the various patient schedules to more adequately average the relative needs of the various patients over the course of the day to thereby provide a more efficient environment, e.g., an environment wherein fewer employees satisfy the needs of the patients The system 100 also displays the employees that are scheduled to work during the day and also displays a value related to number of employees that are scheduled to work and are qualified to satisfy the patient needs, on a per interval basis. Displaying such employee information along with each employee's ability to provide direct patient care, even if partial, provides a quick reference in determining whether an adequate number of capable employees have been scheduled for the day, as discussed in more detail below. The system may also display other activities performed by the employees such as indirect patient care activities and management or other non-patient care activities to provide a relatively complete picture of employees and associated assignments in relation to patient needs and/or facility resources.

Figure 2:
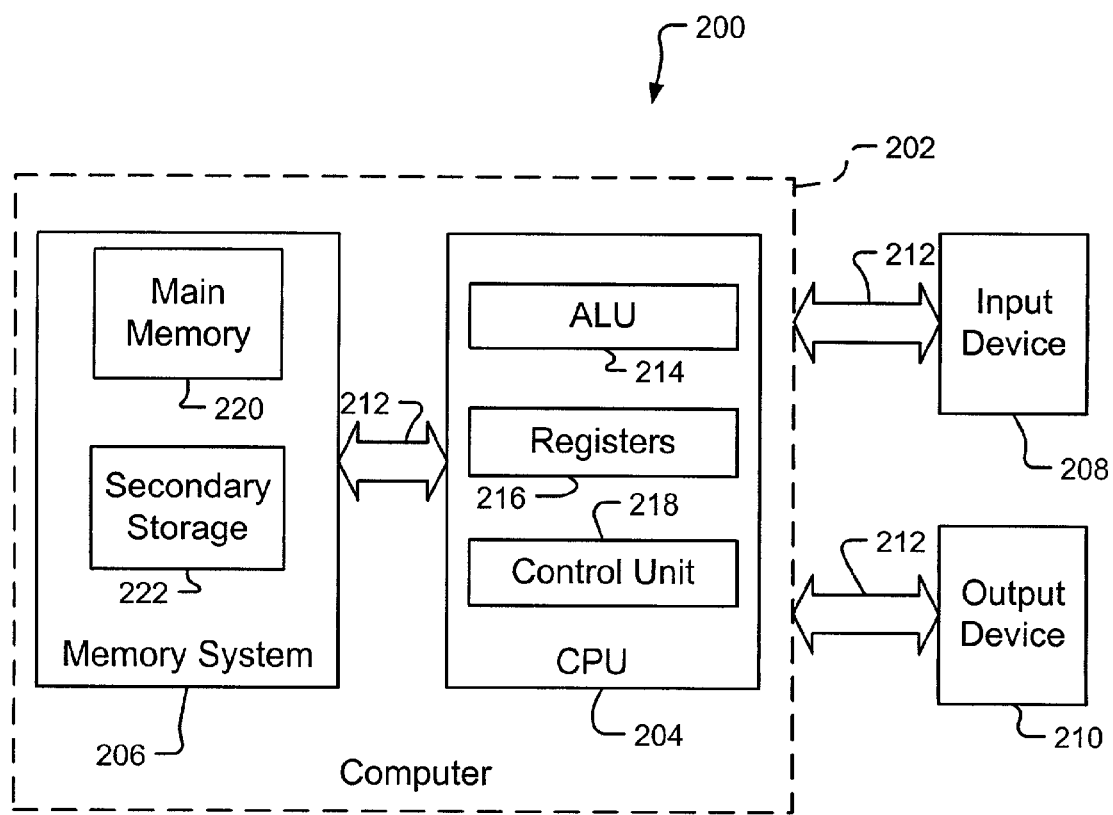
FIG. 2 is a functional diagram of a computer system having a memory that stores information related to patients and employees and a microprocessor to compute needs and requirements that may incorporate aspects of the present invention.

In an embodiment of the invention, the system 100 incorporates at least one computer system, such as computer system 200 shown in FIG. 2. The following discussion, in conjunction with FIG. 2, is intended to provide a brief, general description of a suitable computing environment in which the invention may be implemented. Although not required, the invention is described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including handheld devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

The scheduling system 100 (shown in FIG. 1) incorporates a computer system 200 of computer resources for implementing an embodiment of the invention, as shown in FIG. 2. The system 200 incorporates a computer 202 having at least one central processing unit (CPU) 204, a memory system 206, an input device 208, and an output device 210. These computer resources 206 and 208 are coupled to computer 202 by at least one system bus 212.

The CPU 204 is of familiar design and includes an Arithmetic Logic Unit (ALU) 214 for performing computations, a collection of registers 216 for temporary storage of data and instructions, and a control unit 218 for controlling operation of the system 200. The CPU 204 may be a microprocessor having any of a variety of architectures including, but not limited to those architectures currently produced by Intel, Cyrix, AMD, IBM and Motorola.

The system memory 206 some form of computer readable media. Computer readable media can be any available media that can be accessed by 202. By way of example, and not limitation, computer readable media may comprise computer storage media and communication media. Computer storage media, shown as main memory 220 and secondary storage 222, includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by 202. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media. Memory devices within the memory system and their associated computer readable media provide non-volatile storage of computer readable instructions, data structures, programs and other data for the computer system.

The system bus 212 may be any of several types of bus structures such as a memory bus, a peripheral bus or a local bus using any of a variety of bus architectures.

The input and output devices are also familiar. The input devices 208 can comprise a small keyboard, a touch pad, a touch screen 102, etc. The output devices 210 can comprise a display, such as display 102 (FIG. 1), a printer (not shown), speaker 108, etc. Some devices, such as a network interface or a modem can be used as input and/or output devices. The input and output devices 208 and 210 are connected to the computer through system buses 212 as shown in FIG. 2.

The computer system 200 further comprises an operating system and usually one or more application programs. The operating system comprises a set of programs that control the operation of the system 200, control the allocation of resources, provide a graphical user interface to the user, facilitate access to local or remote information, and may also include certain utility programs such as scheduling software as discussed below. An application program is software that runs on top of the operating system software and uses computer resources made available through the operating system to perform application specific tasks desired by the user. In general, an application is responsible for generating displays and interpreting the user input through the interface input elements.

Although the hardware operating environment is shown in FIG. 2, the present invention may be described in the general context of a software operating environment, e.g., computer-executable instructions, such as program modules, being executed by a computer, such as computer 202. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Figure 3:
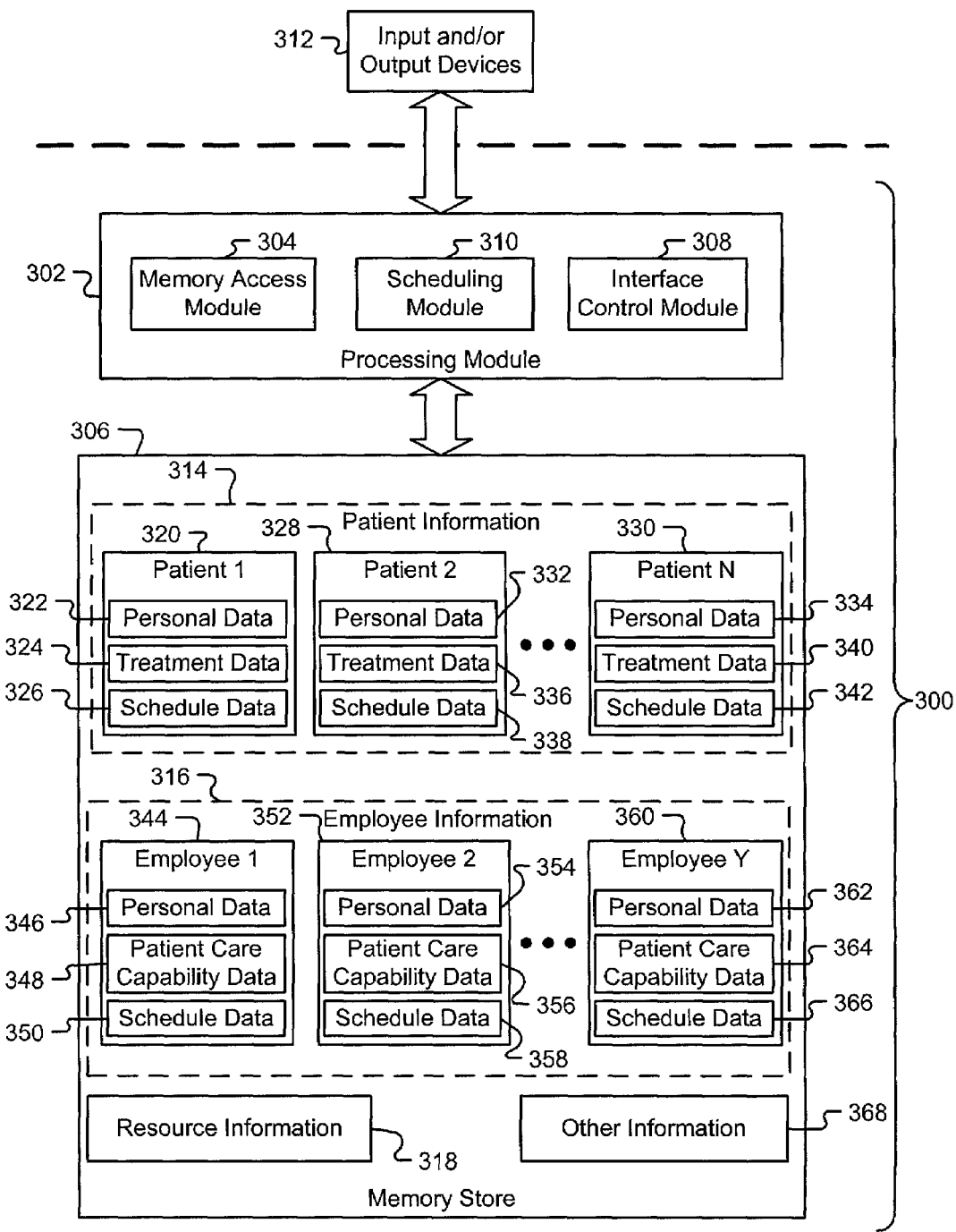
FIG. 3 is a block diagram illustrating software components of the present invention, including a services layer for managing the server-side lock allocation.

FIG. 3 illustrates an example of a software operating environment 300 in which the invention may be implemented. The software operating environment 300 is only one example of a suitable operating environment and is not intended to suggest any limitation as to the scope of use or functionality of the invention. Software environment 300 incorporates a processing module 302 that includes a number of sub-modules used to perform aspects of the present invention. For instance, the module 302 has a memory access module 304 to store and retrieve information to and from a memory store 306. The module 302 also has an interface module 308 that interfaces with the input and output devices 312 (such as input and output devices 208 and 210, respectively, shown in FIG. 2) to receive input information and to produce output information. Additionally, the module 302 has a scheduling module 310 for calculating scheduling information based on information in memory store 306.

The memory store 306 comprises at least three types of information, patient information 314, employee information 316 and resource information 318.

With respect to the patient information 314, in an embodiment, the information is divided into records or profiles wherein each patient has a profile. An example profile is illustrated as 320 for "patient 1". The profile 320 includes information related to the patient, such as personal information, e.g., name, address, sex, birth date, etc., which is illustrated as personal data 322. The profile also has other patient information such as treatment information 324 and scheduling information 326, the combination of the two defining patient requirements for the particular patient. Treatment information 324 relates to the general type of treatment the patient typically needs or receives. The treatment information 324 may further include other restrictions or limitations that a patient may have that impact a clinic in providing direct, indirect or non-patient care in satisfying that particular patient. In a dialysis treatment embodiment, information 324 may relate to the length of treatment, type of medicines used, etc. Hence, the treatment data 324 relates to or provides an employee with the necessary information required to set up and treat the patient during a visit.

The patient profile also includes scheduling information 326, which relates generally to when the patient visits the clinic and the length of time the patient stays during a visit. The information 326 may relate to the number of days a week a patient visits the clinic or possibly, the particular days, e.g., Monday, Wednesday and Friday versus Tuesday and Thursday. The scheduling information 326 may also include information such as whether the patient needs to be scheduled at a particular time, e.g., mornings or afternoons, whether the patient needs extra time during set up and/or following a treatment. Hence, the scheduling information alone or in combination with the treatment data provides the health provider with the necessary information required to allocate clinic resources and employee time during the patient's visit, e.g., while the patient is being treated or is otherwise requiring care.

Patient information section 314 also includes other profiles, such as profiles 328 and 330. Profile 328 relates to information for a different patient than the patient associated with profile 320. Profile 328 has its own personal data section 332, treatment data section 336 and schedule data section 338. Such information sections 332, 336 and 338 are similar to the section 322, 324 and 326 in that each includes the same type of information, respectively, but however, the information for profile 328 is specific to a different patient and therefore, most likely different in content as well.

Profile 330 relates to the last patient profile in the patient information section 314, i.e., "Patient N" wherein the N relates to the number of patients having stored profiles in the memory 306. In some situations, the number of patient profiles may be quite low, e.g., two or three, and in other situations, the number may be higher, e.g., a hundred or more. Moreover, since the store 306 may also store information related to patients that are not necessarily being serviced by the clinic, e.g., deceased patients or temporary patients, the number of profiles may be even higher. Regardless, the profile 330 has a personal data section 334, a treatment data section 340 and a schedule data section 342. If the patient is deceased or temporary, the schedule information section 342 may reflect this information.

With respect to the employee information 316, in an embodiment, the information is divided into records or profiles wherein each employee that works at the clinic has a profile. An example profile is illustrated as 344 for "Employee 1". The profile 344 includes information related to the employee, such as personal information 346, e.g., name, address, sex, birth date, etc., as well as other information such as more information such as patient care capability data 348 and scheduling information 350. Patient care capability data 348 relates generally to the employee's ability to handle direct patient care situations. However, in other embodiments, this information 348 may further include indirect patient care capabilities, such as setting up a machine or taking a machine down, in order to provide the system the ability to monitor the efficiency of an employee with respect to patient care. In a dialysis treatment embodiment for example, information 348 relating to direct and/or indirect patient care may relate to whether the employee is fully trained or in training, whether the employee is handicapped and is therefore limited in some way of providing direct patient care, etc. If the employee is fully trained and is not limited for any reason from providing direct patient care, then section 348 may so reflect. However, if the employee is limited for some reason, then section 348 may likewise reflect such a situation. This information is generally used for scheduling efficiency, i.e., the efficiency of the employees with respect to patient care and an hours per treatment calculation.

The employee profile 344 also includes schedule data 350, which may relate to employee's work schedule, listing the days and times that the employee is scheduled to be at the clinic. However, the data 350 may also include other scheduling information, such as the various tasks that may be performed by the employee, thereby potentially reducing the number of working hours that the employee can devote to direct patient care duties. Hence, the scheduling information alone or in combination with the patient care capability data 348 provides the health provider with the necessary information required to determine an employee's availability and capability while an employee is scheduled to work.

Although not shown, the employee profile 344 may further include information related to activities performed by the employee relating to non-patient care. This type of information may be important in evaluating the overall staff efficiency of an employee and/or a facility. Non-patient care activities may include administrative duties, facility maintenance duties, etc.

Employee information section 316 also includes other employee profiles, such as profiles 352 and 360. Profile 352 relates to information for "Employee 2", i.e., a different employee from the one associated with profile 344. Profile 352 has its own personal data section 354, patient care capability data section 356 and schedule data section 358. Such information sections 354, 356 and 358 are similar to the section 346, 348 and 350 in that each includes the same type of information, respectively, but however, the information for profile 354 is specific to a different employee and therefore, most likely different in content as well.

Profile 360 relates to the last employee profile in the employee information section 316, i.e., "Employee Y" wherein the Y relates to the number of employees having stored profiles in the memory 306, typically relating to the number of employees that work in the clinic or at least the number of employees that may provide direct patient care to patients. Profile 360 comprises a personal data section 362, a patient care capability data section 364 and a schedule data section 366, each of which is similar to the corresponding sections described above with respect to profiles 344 and 352, but having information specific to Employee Y.

Memory store 306 also a resource information section 318, which stores information related to the various resources available, i.e., the facility limitations. These resources may need to be calculated into any scheduling efforts as some resources are limited in that these resources may, in some circumstances, only be used by one patient or employee at a time. For instance, in the dialysis clinic example, the resource information section 318 may relate to the various dialysis machines that can be used at the clinic. Only one patient at a time can typically use these machines at a time. Therefore, when scheduling patients, the availability of these resources should be taken into account.

The memory store 306 may also have other information 368 relating to clinic specific information, such as the store hours, location, etc. The other information section 368 is shown to also indicate that the store 306 may be used to store other information used in scheduling employees and patients that is not explicitly described above.

In operation, the scheduling module 310 schedules patients on a daily, weekly, bi-weekly or other time schedule. The scheduling module 310, using the memory access module 304, accesses the profile for the patient to determine the days and times for treatment, taking into account available resources from resource information section 318. The scheduling module 310 may also use employee information 316 but typically the employees are scheduled at a later time based on patient care needs. The scheduling module 310 stores the information into a calendar-type schedule (not shown) which may or may not be stored in memory store 306. When the patient information section 314 changes, e.g., by adding, modifying or deleting a patient profile, the scheduling module 310 may automatically update the schedule based on the new information. Furthermore, when the resource information 318 or other information 368 changes, e.g., by adding or removing a machine or by changing the operating hours for the clinic, then the scheduling module 310 may automatically update the schedule based on this new information as well.

In an embodiment, the scheduling module 310 may only modify or update the schedule for "today only" such that all future days are not affected and no past days are affected. Such an embodiment may be useful in cases wherein a change is only temporary and no future days should reflect this change. However, in another embodiment, the module 310 modifies the schedule from "today going forward" and thus updates "today" as well as all future days. This embodiment may be helpful when the changes are permanent but when the past days information is used for archival purposes and thus should not be modified. Thus, in this embodiment, past days are not affected, and in order to modify past days, the user must explicitly edit those days. Of course, in yet another embodiment all days may be automatically updated.

In an embodiment of the invention, once the patients are scheduled, then job-types may be scheduled. That is, the user may enter the type of job that should be scheduled for a particular day, e.g., a certified nurse job-type. The job-type provides an indication to the user that once a certified nurse is scheduled then a predetermined number of direct patient care tasks may be satisfied by that job-type. Once the job-type has been scheduled, then the actual employee may be scheduled to fill the shift of the particular job-type. The employee profiles, in this embodiment, provide an indication as to what job-types the employee is qualified to perform. Therefore, in scheduling an employee for a shift of a predetermined job-type, the system may generate a list of capable employees, which further simplifies the process.

Once the patients are scheduled with respect to the various resources, then the employees may be scheduled. In alternative embodiments, the employees are scheduled first. Scheduling the employees relates to evaluating the employee profiles to determine which days the employees are typically scheduled and adding them to the schedule. The schedule for employees is the same as the schedule for the patients, i.e., the schedule includes information for the both the patients and the employees. A user of the system may perform the task of adding employees to a schedule, one employee at a time, or the scheduling module 310 may automatically evaluate each profile and schedule the employees based on the profiles. Typically, a user may then review the schedule and add or subtract employees as necessary so that the clinic is operating at a more optimal level based on employee skill mix or achieve other scheduling goals.

To help the user determine relative efficiency for the clinic, the scheduling module 310 performs an efficiency calculation to determine whether the clinic has the proper or optimal staffing based on the patient care needs. That is, the schedule is divided into fifteen-minute intervals and for each interval, the module 310 determines the relative needs for the patients during that time, and compares that number to the number of employees capable of providing direct patient care to satisfy those needs and then displays a result based on this comparison. Thus, a quick review of the schedule, and in particular the results based on the comparison, provides a user the necessary information to determine whether to add or subtract employees as necessary so that the clinic is operating at a more optimal level. Additionally, the scheduling module 310 may also review the information once a day is complete to determine scheduling and staffing efficiency according to many different formulas and equations, as discussed below. In another embodiment, larger clinics may be sub-divided into smaller groups and records may be generated related to these different sub-groups. In fact, the sub-groups may edit and view their information separate from the rest of the clinic. In such a case, the overall clinic efficiency report would relate to a combination of the sub-group calculations.

The exemplary operating environment having now been discussed, the remaining part of this description section will be devoted to a description of the operative modules embodying the invention and screenshots relating to a particular embodiment of the invention. The logical operations of the various embodiments of the present invention are implemented (1) as a sequence of computer implemented steps or program modules running on a computing system and/or (2) as interconnected hardware or logic modules within the computing system. The implementation is a matter of choice dependent on the performance requirements of the computing system implementing the invention. Accordingly, the logical operations making up the embodiments of the present invention described herein are referred to alternatively as operations, steps or modules.

Figure 4:
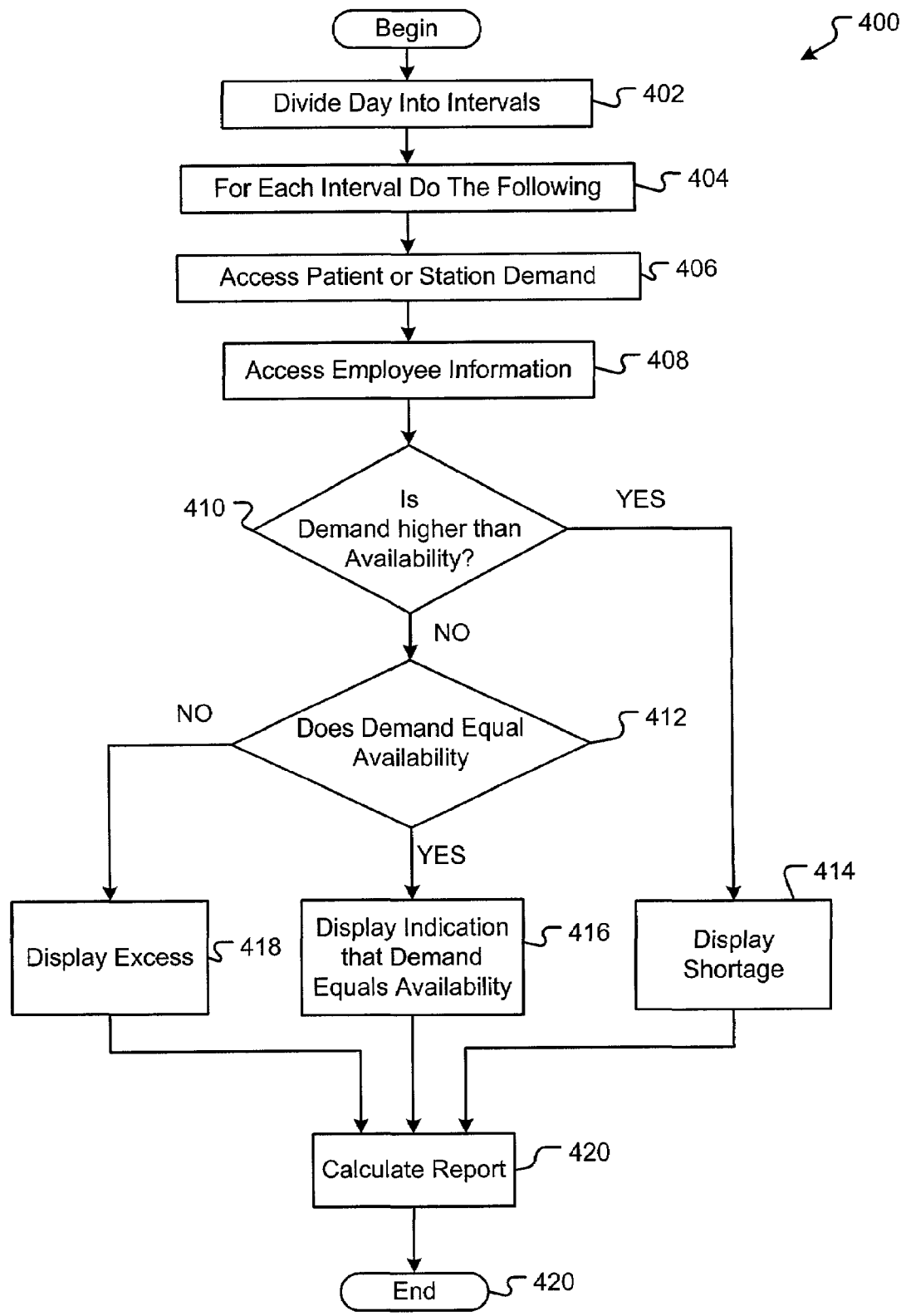
FIG. 4 is a flow diagram illustrating the functional components of scheduling patients and employees according to the present invention.

FIG. 4 is a flow chart of the operational characteristics related to scheduling patients and employees in a health care environment wherein the patients have predetermined needs and employees have predetermined capabilities in tending to the patients. Process 400 begins following the entering of the patients and employees into a schedule according to techniques described above. That is, the user of the system enters patient information into profiles and then schedules various patients for each day. Additionally, the user may schedule some employees to work for each day. Once a patient has been entered into the schedule, then the process 400 begins.

Initially, since the schedule is divided by days, each day is further divided into smaller intervals at operation 402. In an embodiment, the interval length is fifteen-minute intervals. Of course, almost any length of time may be used in creating these intervals, but the time should be small enough to provide meaningful information relating to the various activities of a particular day.

Following divide operation 402, the process 400 evaluates various elements on a "per-interval" basis, as indicated by 404. Hence, for each interval, access patient demand operation 406 accesses the demand of the patient(s) that have been scheduled in the particular interval. Determining the patient demands for the interval relates to evaluating the profile for the patient that is scheduled for treatment during that time interval. The profile gives general information, such that the patient may need approximately one hour and thirty minutes of attention over a four-hour treatment time. However, if the patient treatment time falls within the given interval, then it may be determined that the patient needs the full attention of an employee during that interval. In this example, the needs of that patient, although only one hour and thirty minutes worth, may be deemed to require attention during a full four-hour period, i.e., four hours worth of employee attention.

However, in an alternative, preferred embodiment, it is determined that the patient needs the attention of 37.5% of an employee over the course of the four-hour period, for a total of one hour and thirty minutes. In this embodiment, the needs for the patient are given a value of 0.375 or three-eighths during the interval (and all other intervals spanning the four-hour period.) By only determining that the needs are 0.375, the overall value is more accurate, and the employee scheduling may be more optimal. Obviously, a person cannot be in two places at one time, but in certain situations, the employee can evaluate the requisite needs of the various patients and attend to them one after another.

In the case where the employee tasks are relatively fixed in time, such that the employee does not have discretion as to when the task must be performed, e.g., setting up a dialysis station for use by a patient at a particular time, then the schedule may reflect this situation as a value of one during that time interval. As shown in operation 406, station demands, such as setting-up, taking-down, disinfecting, etc. may also be determined at operation 406. Thus operation 406 generally determines the number of employees that need to be staffed during a particular interval—taking into account that some tasks may be spread over more than one interval by assigning fractional values. Adding the various fractional and whole values provides an overall number of employees needed. A rounding step at the end may be necessary in this case to round up any partial number to make sure enough employees are scheduled. For example, if it is determined that during an interval, 2.5 employees are required to perform the tasks of the interval, then the value is rounded up to three, as it actually takes three people to perform the work of 2.5 people. In an embodiment, this determination is displayed on an output device.

Upon determining the various needs of the patients and stations, access employee information operation 408 determines the currently staffed employee capabilities for each interval. As was the case with the task determination 406, employee information may relate to partial values, wherein an employee is counted at a value less than one for some reason, such as the fact the employee is in training, handicapped, or otherwise assigned to other duties during the day. The employee profiles provide the necessary information for each employee. Alternatively, when the employee is scheduled, the employee may be assigned various tasks, such as direct patient care or some other tasks. Once assigned, the method determines whether the employee is capable of performing the tasks (by checking the employee profile) and then provides a message if the employee cannot perform the tasks or otherwise provides a reduced value if the employee can only perform the tasks at a less than full value. These whole or partial values are added to determine an overall number of available and capable employees during each interval. Again a rounding step is performed at the end. The value may be rounded up or down. Rounding up may be preferred in some cases since the rounded value provides an indication as to the total number of people working. However, in other embodiments, rounding down may be preferred so as not to provide a false indication of the number of available employees during an interval. In an embodiment, the rounded-down value is displayed on an output device.

Following the access employee information operation 408, then determination act 410 determines whether, for each interval, the demand is higher than the employee availability. Determination act 410 may determine whether the demand is higher by simply subtracting one from the other or otherwise comparing to the two summed values. In making the comparison, determination act uses the actual summed values relating to the demands and the employee availability, as compared to the round numbers. Thus, determination act 410 may determine that, for a particular interval, there are too many employees scheduled or too few. The value is rounded to the nearest whole person and displayed.

For instance, if determination act 410 determines that demand is higher than availability, then display operation 414 displays the shortage. In an embodiment if the shortage value indicates a shortage by any partial or whole value, then that value is rounded to the nearest whole value to indicate the relative shortage. For example, if the value indicates a shortage of 0.1 or 0.01 persons, then display 414 operation displays a shortage of one employee. As another example, if the value indicates a shortage of 2.2 or 2.9, then operation 414 displays a shortage of three employees. Thus, any partial shortage rounds up to a whole value shortage for display purposes. In an embodiment of the invention, the actual values may be displayed, leaving it up to the user to determine whether to add the proper number of new employees based on the actual values. These values are displayed for each interval of the day. In an embodiment, the value is displayed in red or some other representative color so as to provide an indication that the number relates to a shortage of employees for that interval.

If, however, determination act 410 determines that demand is not higher than availability, then flow branches NO to determination act 412 which determines if the demand equals the availability. If so, then flow branches YES to display operation 416 which displays a zero or some other indication that the availability and demand are equal. In such a situation, the staffing is considered to be optimal for the clinic during that interval. In an embodiment, the value is displayed in black or some other representative color so as to provide an indication there is no excess or shortage of employees for that interval.

If determination act 412 determines that the demand is not equal to availability, then availability is higher than demand, which indicates an excess in employee availability. In such a case, flow branches NO to display operation 418 which displays such an excess. Again, the actual values are used in determining the excess so that the display may either display the actual values or a rounded version of the excess. Typically, the excess values are rounded down to the nearest whole persons, conservatively indicating that the number of additional employees scheduled for a particular interval. In an embodiment, the value is displayed in blue or some other representative color so as to provide an indication that the number relates to an excess of employees for that interval.

In one embodiment, following display operations 414, 416 or 418, calculate report operation 420 determines the relative efficiency for each day. The efficiency calculation generally indicates the relative efficiency of the clinic given the sum values of demand and the sum values of employee availability. Efficiency increases as the two sum values, for demand and availability, converge. That is, when the demand and the availability for the day are equal, then the clinic is operating at 100% efficiency. In alternative embodiments, advanced calculations may be performed to determine efficiency and to calculate and generate various efficiency reports, as described below. Following the calculation of the report, a percentage value may be displayed so the overall efficiency for the day may be viewed while a user performs the task of scheduling patients and staff. Alternative embodiments however, do not calculate or display the efficiency report.

Figure 5:
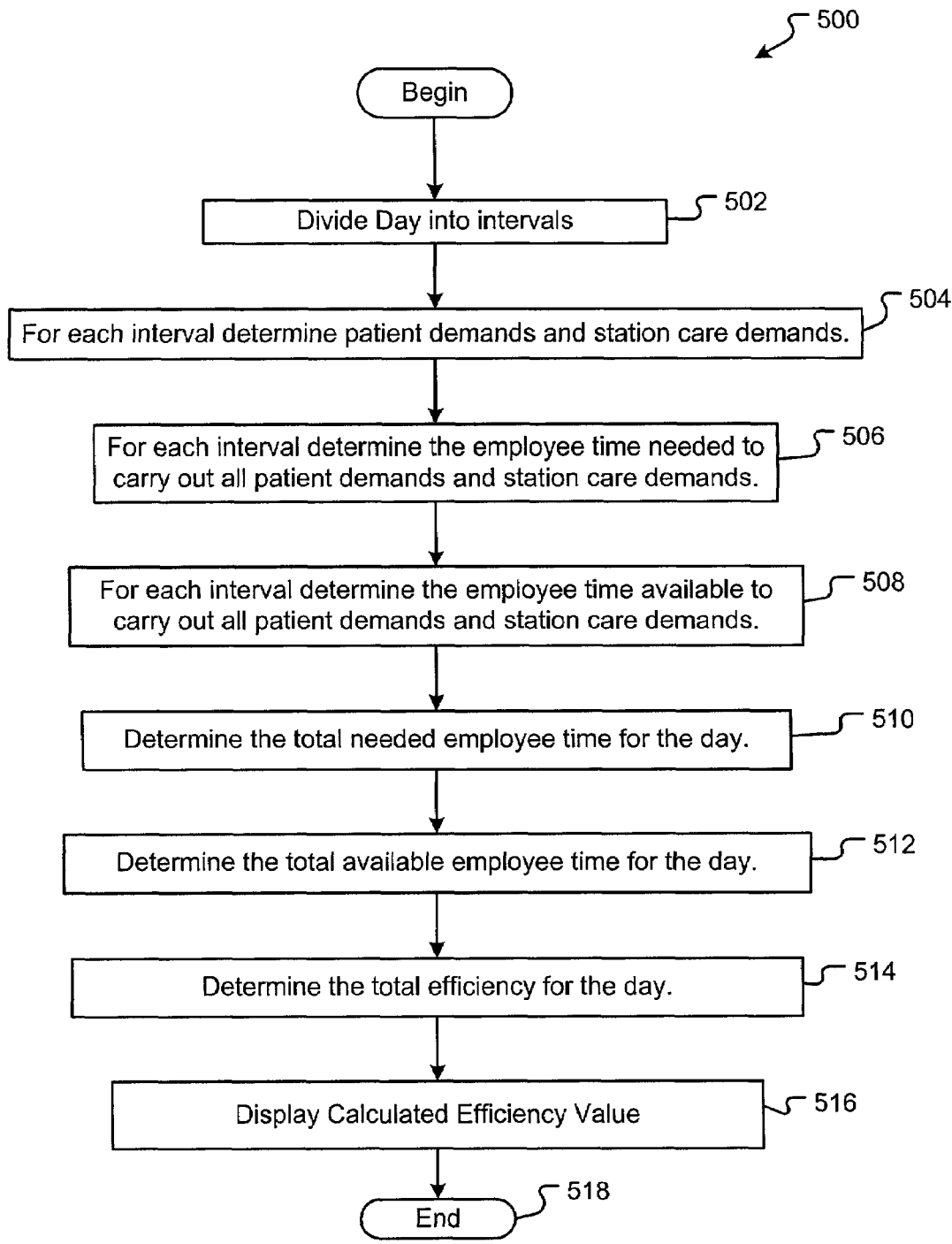
FIG. 5 is a flow diagram illustrating the functional components of determining efficiency in an embodiment of the invention.

In accordance with other aspects of the present invention, the efficiency calculation is relatively complex and relates to various separate calculations. FIG. 5 is a flow chart of the operational characteristics related to determining the efficiency for a particular day having various station and patient demands as well as various employees scheduled for the day. Flow 500 begins as divide operation divides the particular day into numerous intervals, e.g., fifteen-minute intervals. Following divide operation 502, determine operation 504 determines the patient demands and station care demands for each interval. Determine operation 504 is similar to operation 406 shown in FIG. 4 and described above. Upon determining the needs of the patients and the stations, the employee time needed to satisfy these demands may be determined at operation 506.

Following the determination of the needed employee time for each interval, the available employee time for each interval may be determined. The available employee time may be determined from the employee profiles or from the job description as scheduled. Determination operation 510 is similar to access operation 408 described above in that it determines employee availability for each interval. In an embodiment, the number of hours available is decreased by other factors, such as breaks, lunches, etc. These deductions are blended into the average time for an employee in determining efficiency and not into actual availability for patient care since the lunches and breaks may be taken at variable times in the day.

Upon the determination the employee time that is available for a particular day, then determine act 510 determines the total employee time needed for the day in order to satisfy the demands of the patients and the stations. This value may be the summation of the all interval values determined at operation 506. Similarly, the next operation, determination operation 512 determines all the total available employee time for the day. This determined value may be the summation of interval values calculated at operation 508.

Using the summation values from operations 510 and 512, determine operation 514 may calculate the efficiency for the day. In an embodiment, the number of needed employee hours is divided by the number of available hours to determine an efficiency value percentage. Other embodiments may perform yet other calculations to determine the overall efficiency.

Once efficiency has been determined, display operation 516 may display the efficiency value. Following display operation 516, flow 500 ends at end operation 518.

FIGS. 6-25 illustrate screen shots from a particular embodiment of the present invention. The screen shots illustrate various aspects in scheduling patients have specific needs and employees, the employees also having specific needs or capabilities. The embodiment shown in FIGS. 6-25 relate to scheduling patients and employees in a health care clinic that provides dialysis treatment to the patients. Although shown and described with respect to health care, and in particular dialysis clinics, the present invention may be utilized in other businesses as well.

Figure 6:
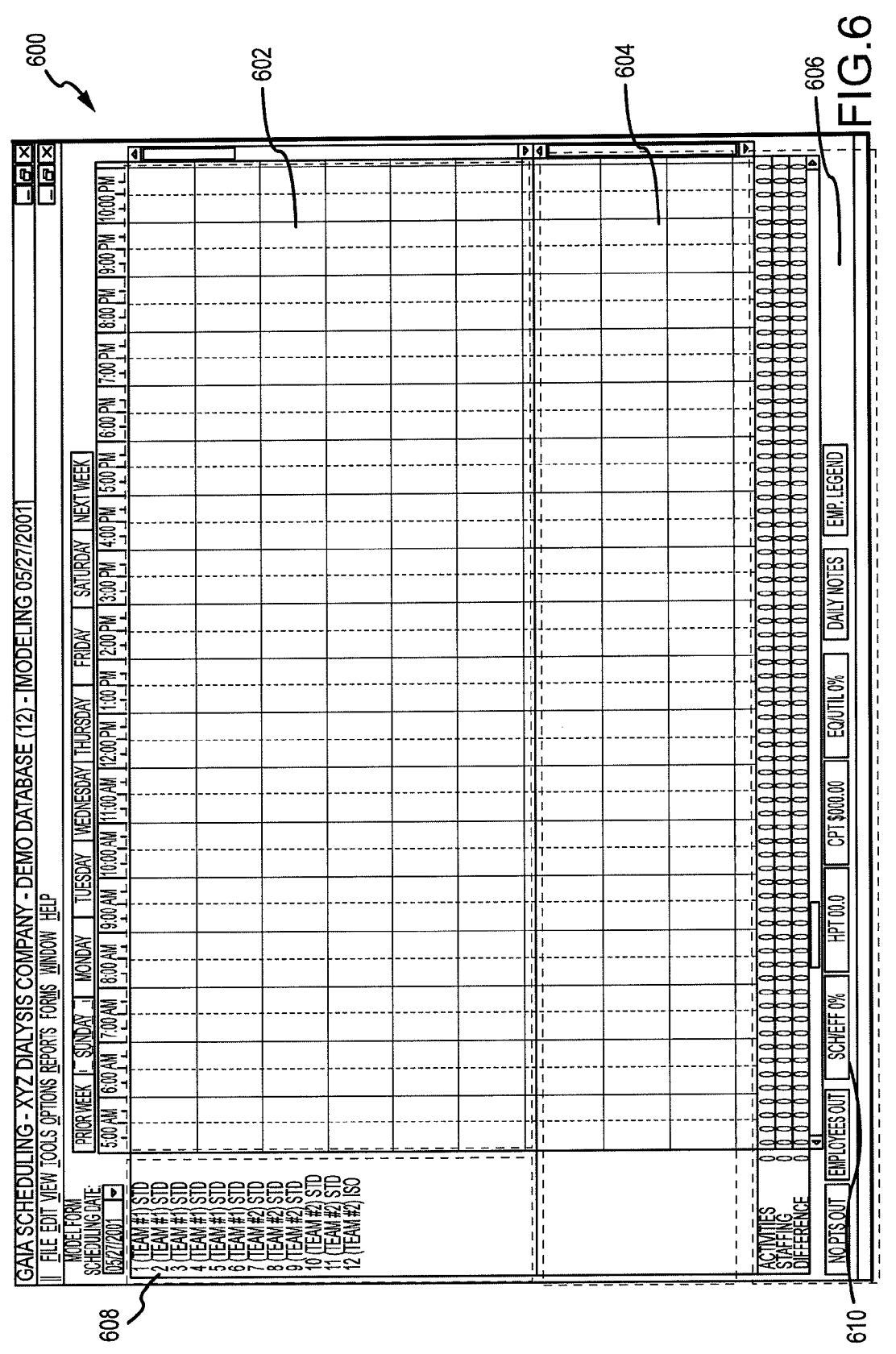

With respect to FIG. 6, the screen shot 600 illustrates the general layout of the graphical user interface for the scheduling system. The system provides a patient scheduling area 602, an employee scheduling area 604, a calculation display are 606, station display 608, among other items. The patient scheduling area 602 provides a visual indication of the patients that are scheduled and for which station. The time values are above the patient scheduling area. As patients are scheduled, the area may also provide as an input system to add or modify patient schedules using known drag and drop techniques. Additionally, the area may be used to generate pop-up menus or windows to further modify or update patient schedules. Similarly, the employee scheduling area 604 may also be used to provide input using a mouse or other computer input systems or techniques. The calculation area 608 is generally a display only region and displays various calculations related to demands and availability for each interval. The area 608 may also have an efficiency display 610, which displays the results of an efficiency calculation for the day.

Figure 7:
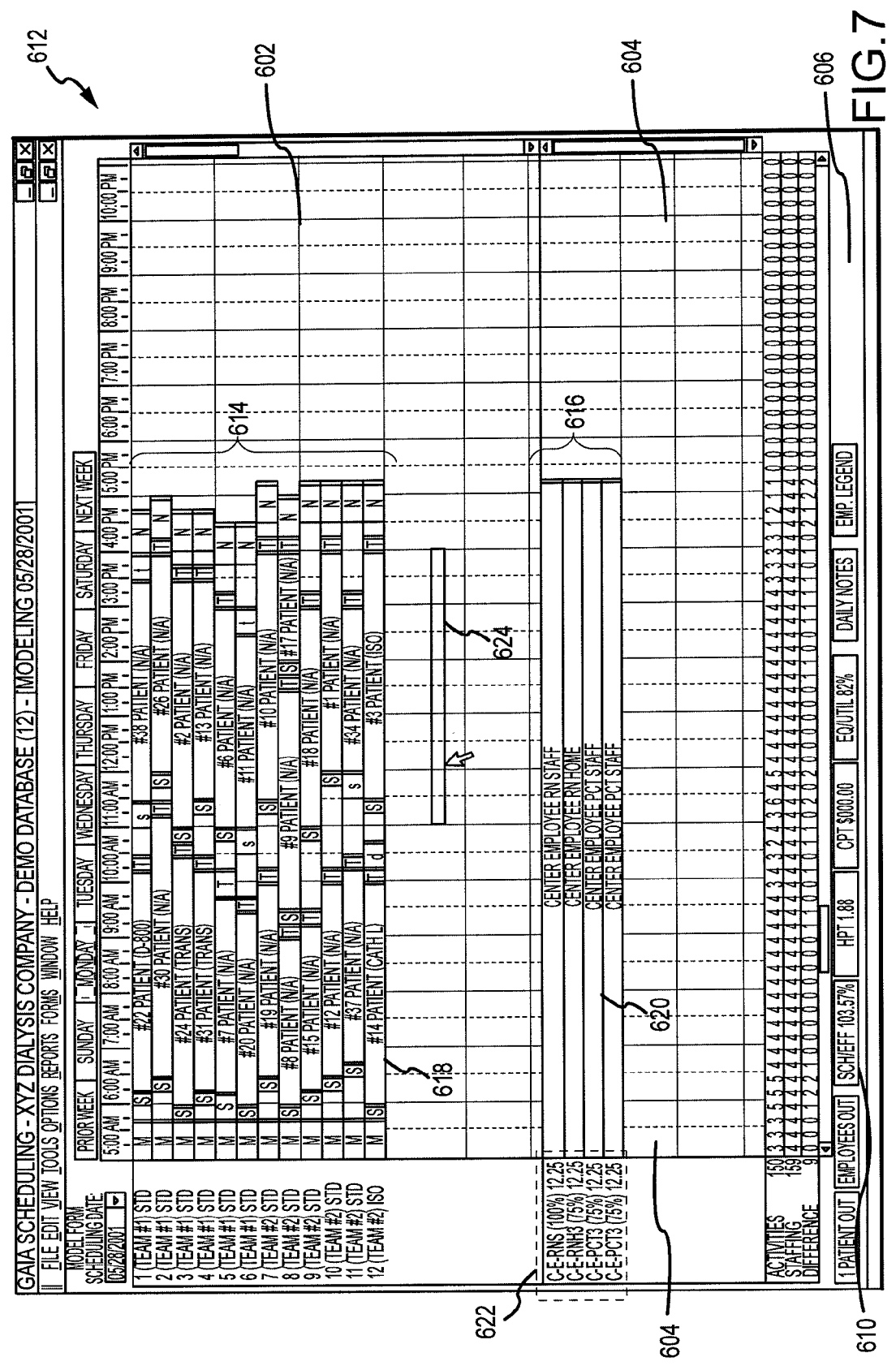

FIG. 7 illustrates screen shot 612 which has the same layout as screen shot 600 shown in FIG. 6 but further includes exemplary patient schedules 614 and employee schedules 616. Each patient schedule portion, such as patient portion 618 relates to the scheduled time for a particular patient. For example, the time scheduled for the patient represented by portion 618 starts at approximately 6:30 AM and concludes at approximately 10:30 AM. The portion 618 may be further broken down into subportions, such as the beginning setup portion indicated by the "S" or the ending portions: "takeoff" stage indicated by the "T" or the disinfect stage indicated by the "d". These sub-portions relate to station demands that are not necessarily patient specific or considered patient care. However, these items require employee attention and are therefore scheduled for this reason.

In editing the patient scheduling portion 602, the portions, such as portion 618 may be selected using a mouse or other computer input system. During a drag and drop procedure, a shadow box 624 is displayed to indicate that drag operation is occurring. Additionally, the shadow box maintains the width of the original portion so as to allow the user to quickly determine whether a drop into a new time zone can be achieved without causing a time conflict with another scheduled task or portion.

The employee portion 604 includes several employee schedules 616 as shown in FIG. 7. The employee schedule portions, such as portion 620 may be moved using a drag and drop technique or the portion may be selected and then edited from a menu or pop-up window. Other techniques may also be employed in adding, modifying or updating the portion 620.

The employee portion 604 also has an information section 622 that provides information relating to each employee that is scheduled. For example, the information section 622 includes the title of the employee and the percentage of time that the employee is dedicated or available for direct patient care duties. Importantly, if the employee is only partially available, i.e., less than 100%, then this information is displayed in the section 622. Additionally, the total hours available for direct patient care may also be displayed, that is, the number of hours the employee is scheduled multiplied by the percentage available. Information section 622 provides a user with a quick reference section to see the percentage of time an employee is available for direct patient care. In an embodiment, the information displayed in section 622 relates to job type, e.g., a manager or a trainee, and not necessarily to the specific employee. In other embodiments, the information may relate to the specific employee and his/her limitations.

Figure 8:
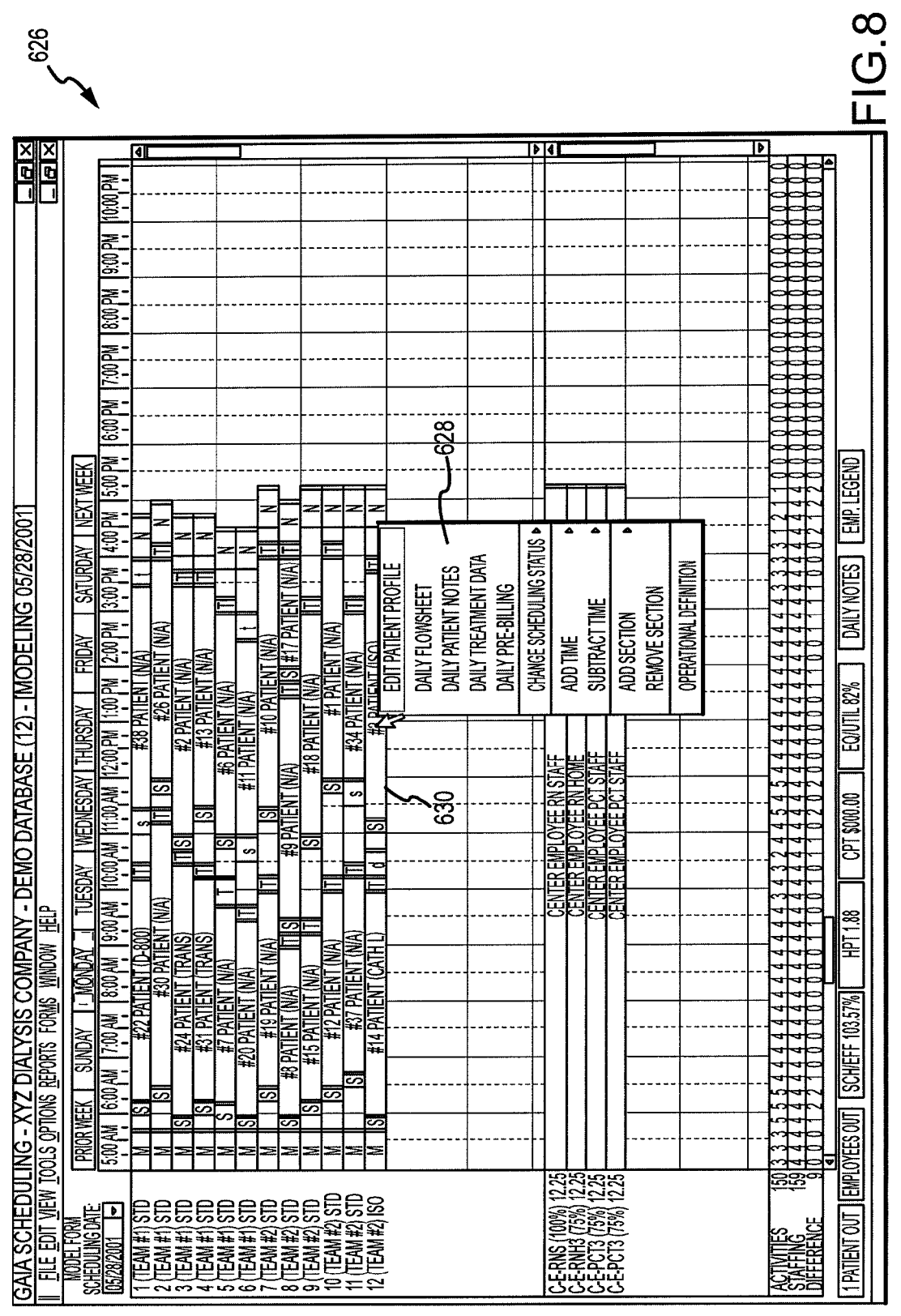

FIG. 8 illustrates a screenshot 626 similar to the screen shot 612 shown in FIG. 7. However, screenshot 626 illustrates a pop-up menu 628 generated by placing the cursor over a patient scheduling portion, such as portion 630 and depressing the right mouse button on the mouse input device. Alternative embodiments may generate the pop-up menu 628 in other ways, such as through the use of a predetermined series of keystrokes. The menu 628 provides a number of options to the user such as adding or subtracting time to the patient appointment portion 630. The menu 628 also provides a means for viewing or editing daily sheets such as a flowsheet, patient notes sheet, treatment data, or pre-billing. The menu 628 may further provide means for adding or removing sections to the appointment or to change the scheduling status. If some of the menu options are not available, then they may be displayed in a "grayed out" manner and selecting them has no effect.

Figure 9:
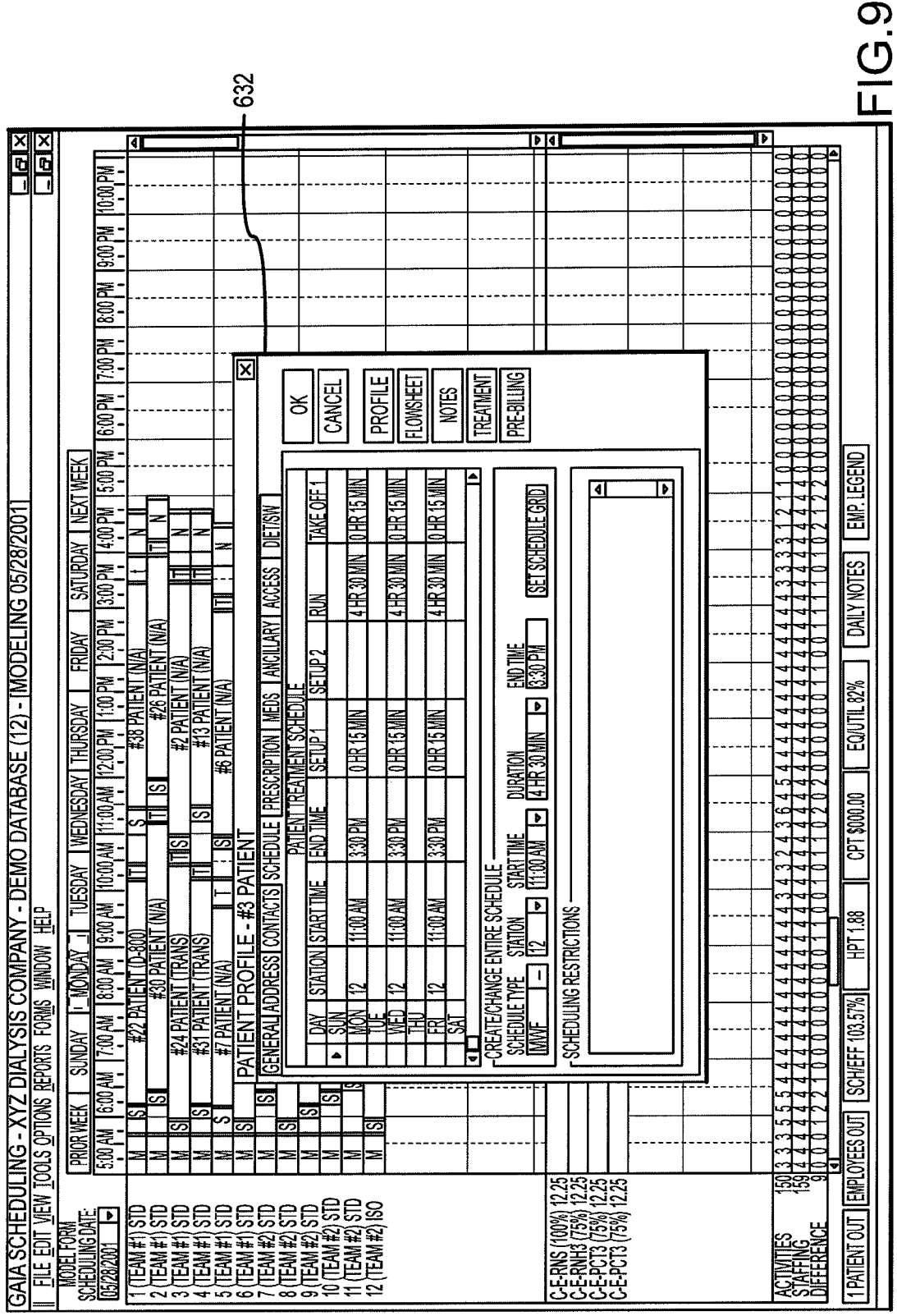
FIG. 9 is a screen shot diagram of a patient profile window for entering the profile of a patient that may be scheduled according to the present invention according to an embodiment of the present invention.

The pop-up menu 628 also provides a method of editing the patient profile for the patient associated with the portion 630. Indeed, one of the menu options is labeled "Edit Patient Profile," and selecting this option generates a pop-up window 632, as shown in FIG. 9. The window provides the user a means of entering and modifying patient information. The various types of information include personal data, treatment data and scheduling data. Once finished, the user may select the OK button to exit the profile modification window 632.

Figure 10:
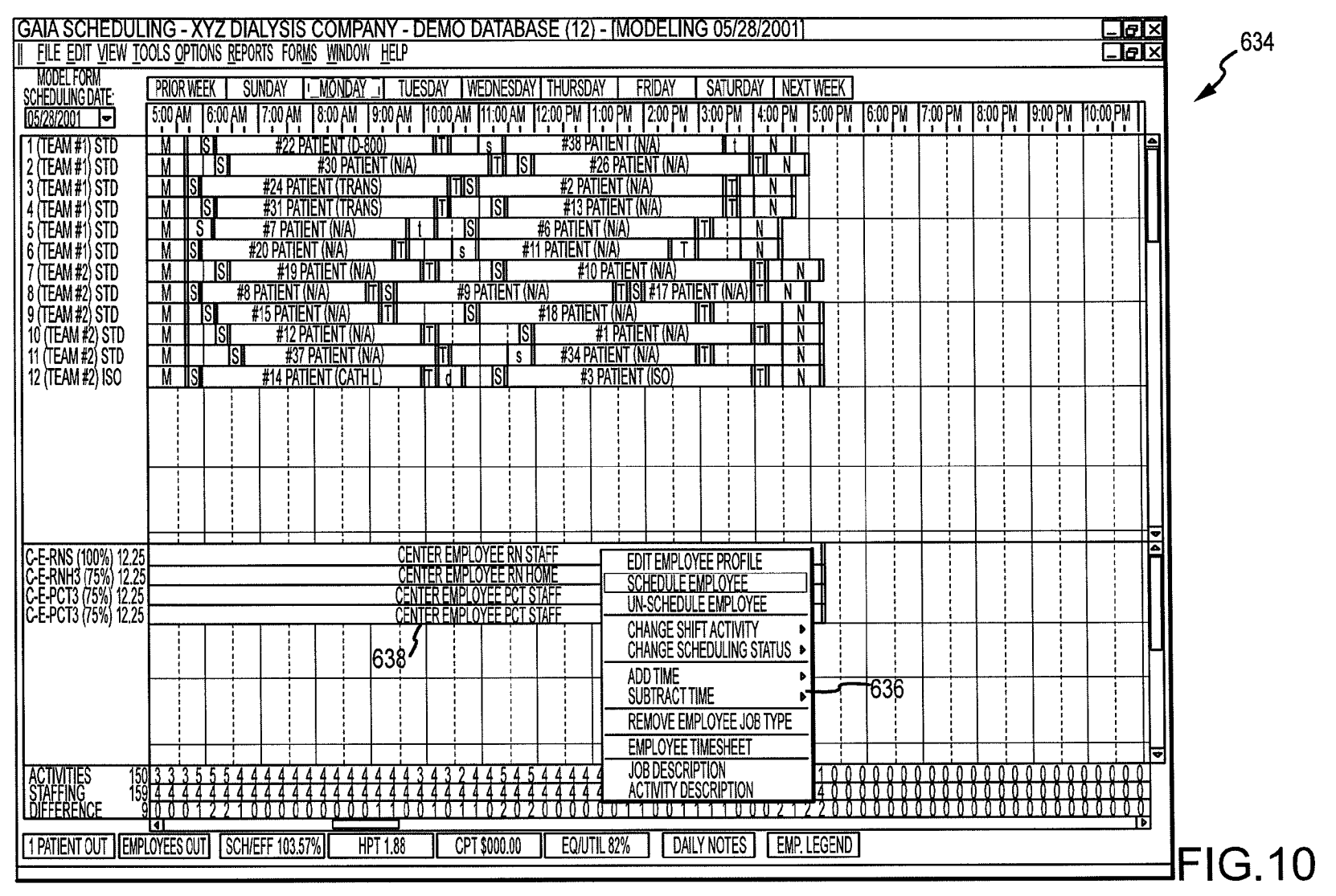

FIG. 10 illustrates a screenshot 634 similar to the screen shot 626 shown in FIG. 8. However, screenshot 634 illustrates a pop-up menu 636 generated by placing the cursor over an employee scheduling portion, such as portion 638 and depressing the right mouse button on the mouse input device. Again, alternative embodiments may generate the pop-up menu 636 in other ways, such as through the use of a predetermined series of keystrokes. The menu 636 provides a number of options to the user such as adding or subtracting time to the employee shift portion 638 or removing the job type completely for the day. The menu 636 also provides a means for changing the shift activities or scheduling status.

In an embodiment, the job shift 638 may relate to a job type or title and not necessarily to a particular person. In a particular embodiment, the various job types may be stored and edited from a pop-up window 640 shown in FIG. 11. Each job type provides a percentage related to the amount of direct patient care associated with the particular job type. That is, an employee that is categorized with a particular job type is considered to be available to provide direct patient care to the extent represented by this value.

Since the employee shift 638 may only relate to a generic job type, the menu 636 (FIG. 10) may further provides means for selecting a particular employee to work during the shift 638. Choosing the "Schedule Employee" option from menu 636 generates pop-window 642, shown in FIG. 12. Window 642 illustrates all potential employees that have been characterized as being able to fulfill the requirements of the particular job type associated with the shift 638. Thus the user may simply select one of the employees from the list to schedule the employee.

Once scheduled, the shift portion 630 shown in FIG. 10 then relates to the particular scheduled employee. In such a case, the menu 636 would provide a menu option relating to editing the employee profile for the scheduled employee. Such a profile relates to the characterizations, e.g., job types, that the employee is capable of doing. The profile may also include other information, such as personal data or specific patient care capability data.

Figure 13:
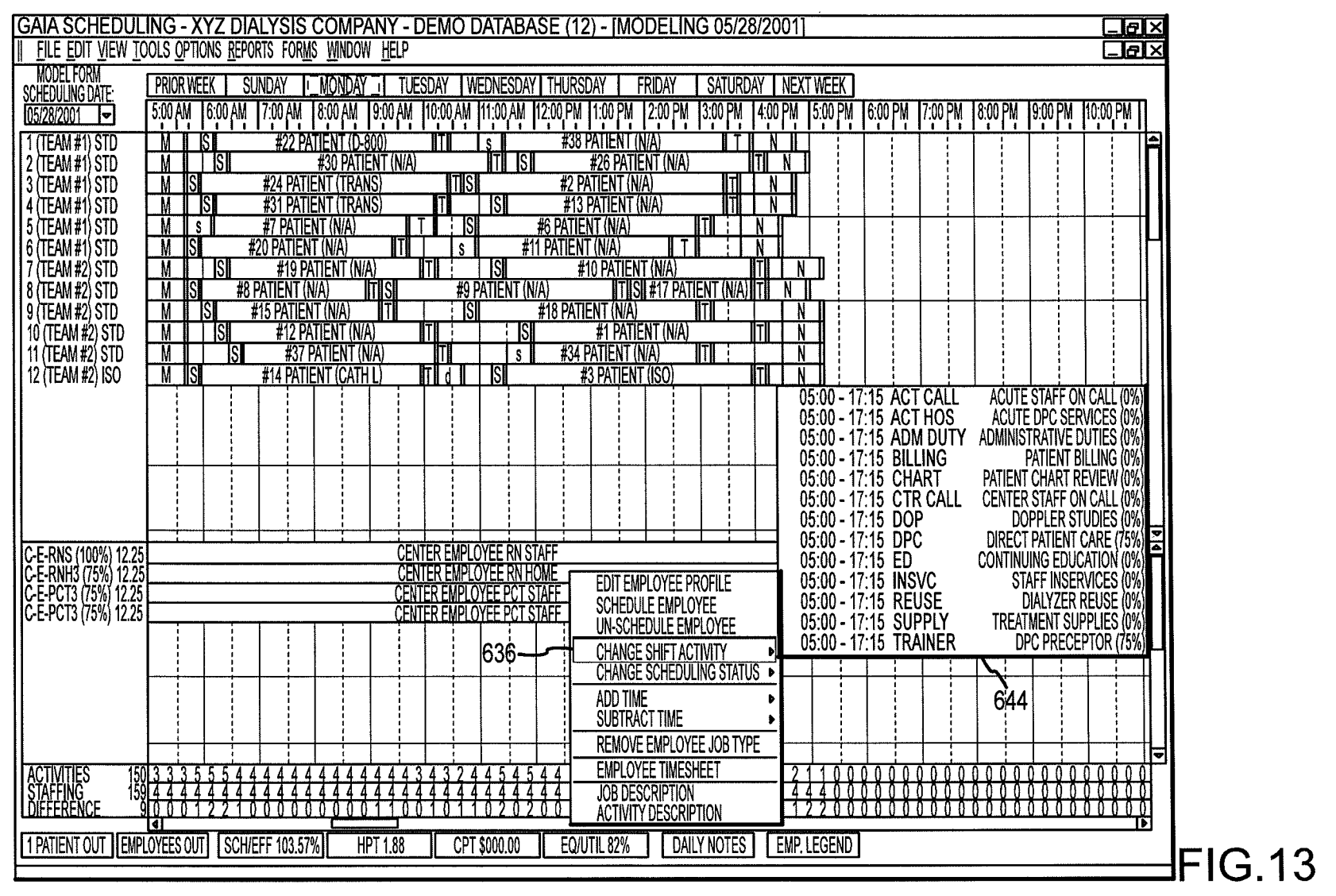

FIG. 13 illustrates yet another option presented by menu 636, i.e., the change shift activity option. Choosing this option generates and displays a cascade menu 644 of various predefined activities that may be assigned to the employee during the shift, wherein each employee is assigned only one such activity for the shift. Each activity has a direct patient care value (in a percentage form) relating to the available direct patient care time the activity provides. Thus, in scheduling employees, the menu 644 provides a quick reference to the amount of direct patient care the employee may provide to patients during his/her shift.

In another embodiment, different activities may be assigned to a shift for different blocks of time. Indeed, the shifts may be sliced in many different ways and activities can then be assigned for each different slice. For example, a particular shift may be assigned to perform direct patient care (at either 100% or at 75%) for the first and last three hours of the shift wherein the middle two hours of the shift are allocated to performing training or some other type of activity. In this case, since the values relating to direct patient care capability at the bottom of the display reflect the activities assigned on a per-interval basis, the efficiency and adequacy of the staffing may be determined in light of the sliced staff schedule portion.

Figure 14:
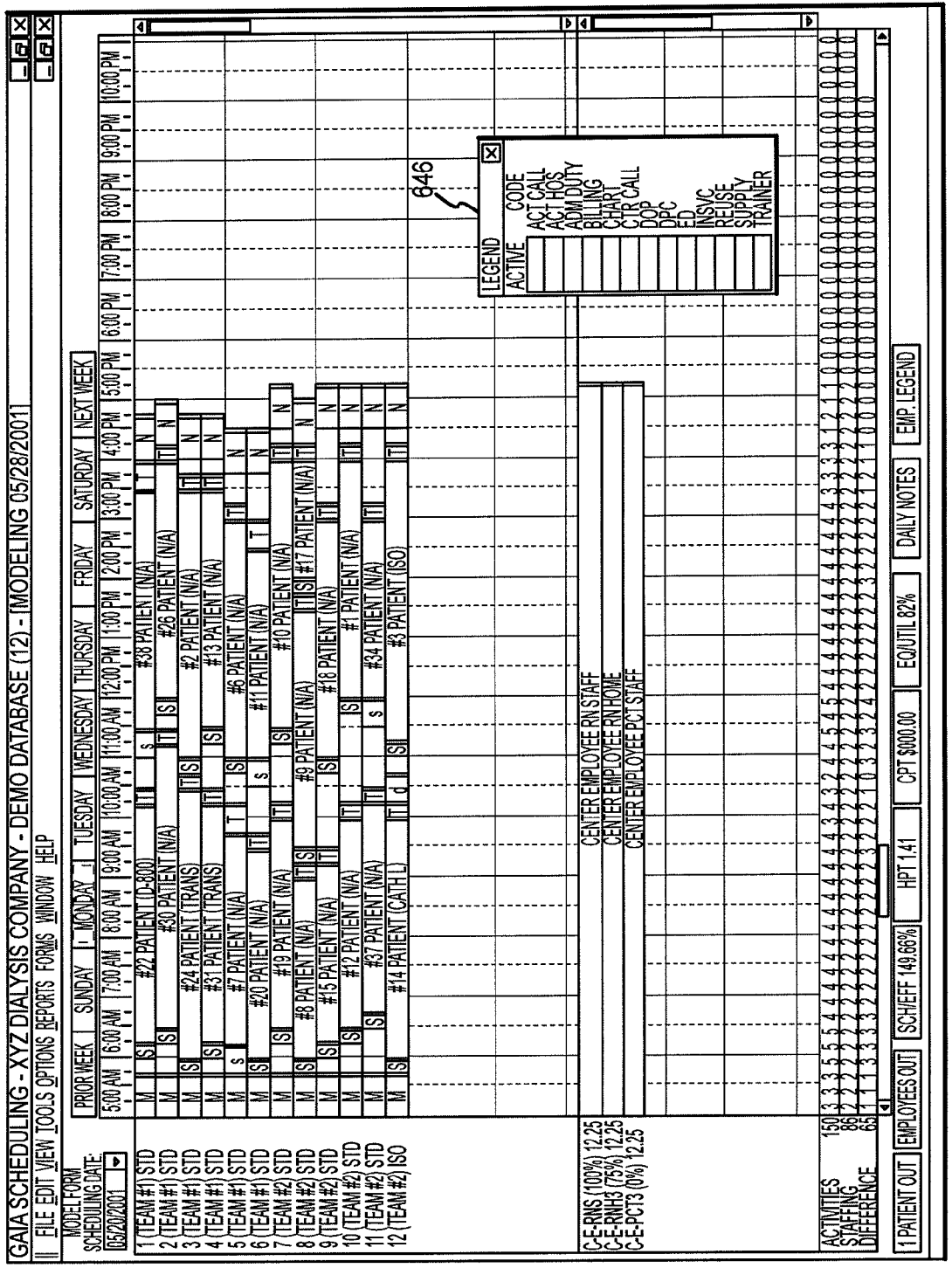
FIG. 14 is a screenshot diagram illustrating a legend of colors indicating assigned shift activities according to an embodiment of the present invention.

As the activity is modified according to the menu 644 (FIG. 13), the employee shift may be displayed in a new color, indicating the assigned shift activity. The colors may further be defined or edited from a pop-up window 646 as shown in FIG. 14. The colors are primarily to provide a simple and relatively quick reference as to the assigned shift activity for the employee. Other colors and/or other techniques may also be used to provide a quick reference.

Figure 15:
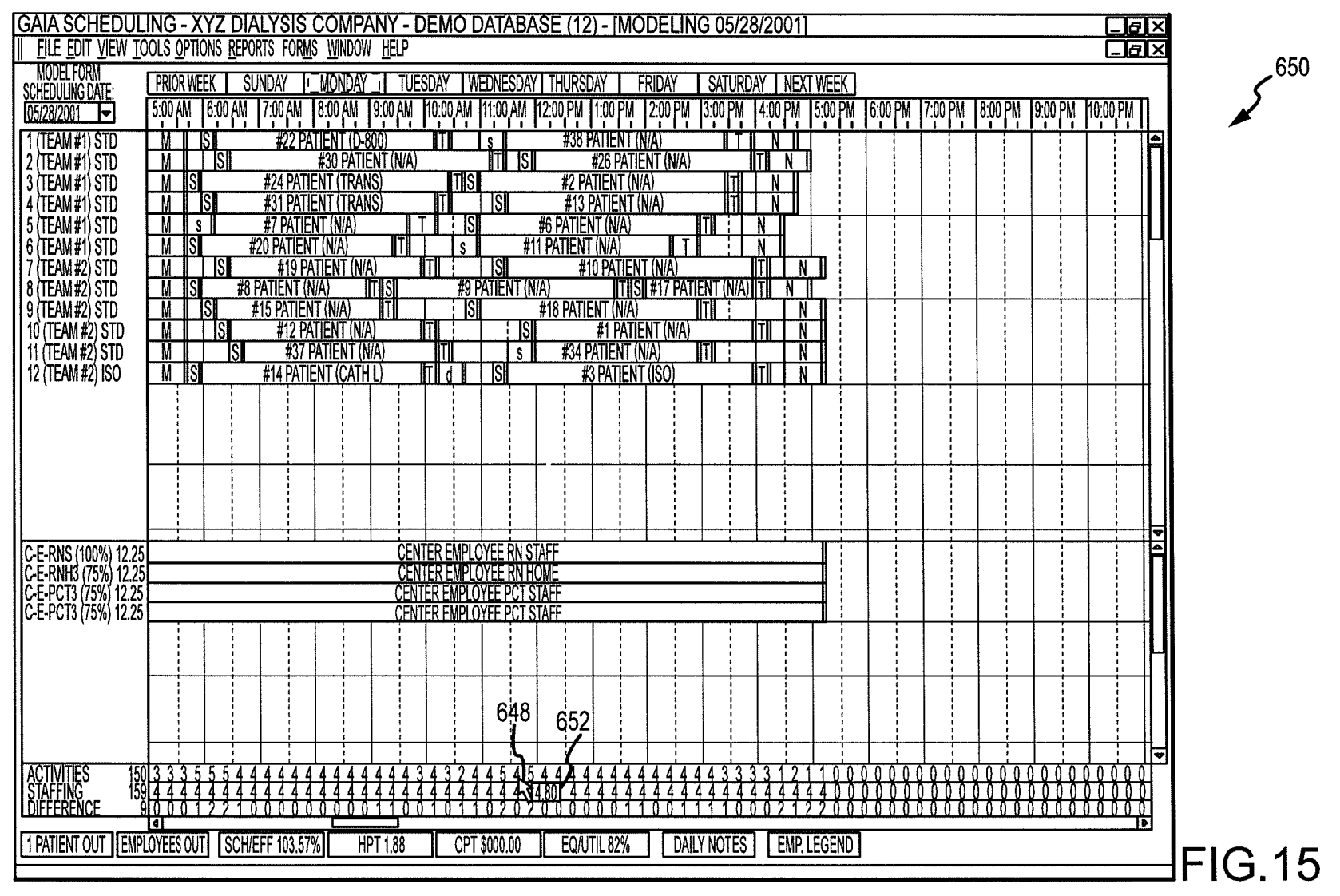

In an embodiment of the invention, when the pointing cursor 648, either controlled by a mouse, trackball or some other input control device, is positioned over an element on the display, such as display 650 shown in FIG. 15, an information box 652 may be displayed. In an alternative embodiment, such display is only provided following a predetermined delay period that the mouse has remained over the element, such as one of the displayed number values. In a particular embodiment, the displayed number values relate to the number of employees required to satisfy the patient needs for each interval, the number of available employees scheduled to satisfy the patient needs for each interval and the difference between the two. As discussed above, the patient needs and the employee availability may be calculated as fractions and thus the actual displayed values are the rounded version of the actual value. However, information box 652 may be configured to display the actual value so the user may readily determine such information.

Figure 16:
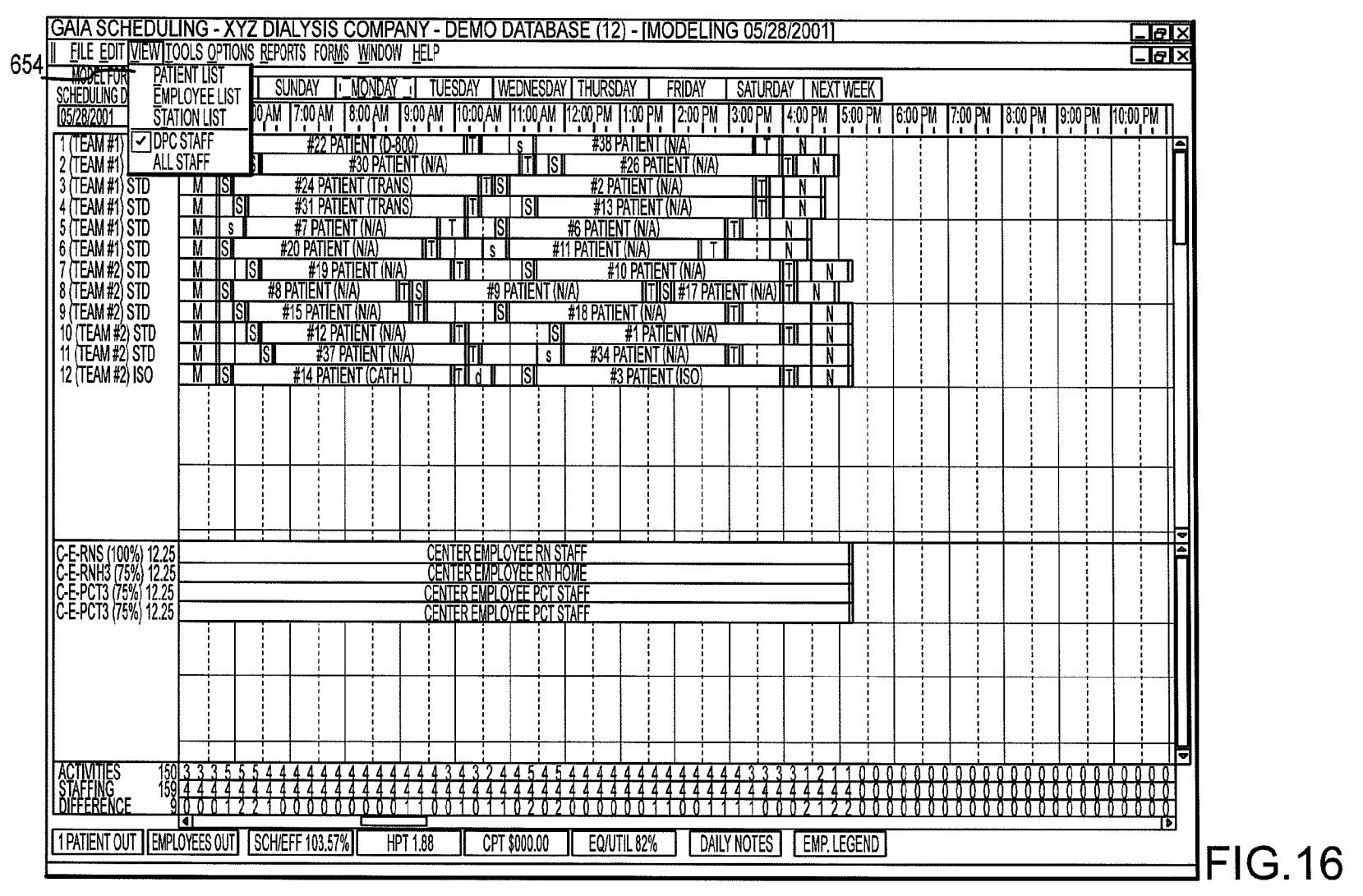
Figure 17:
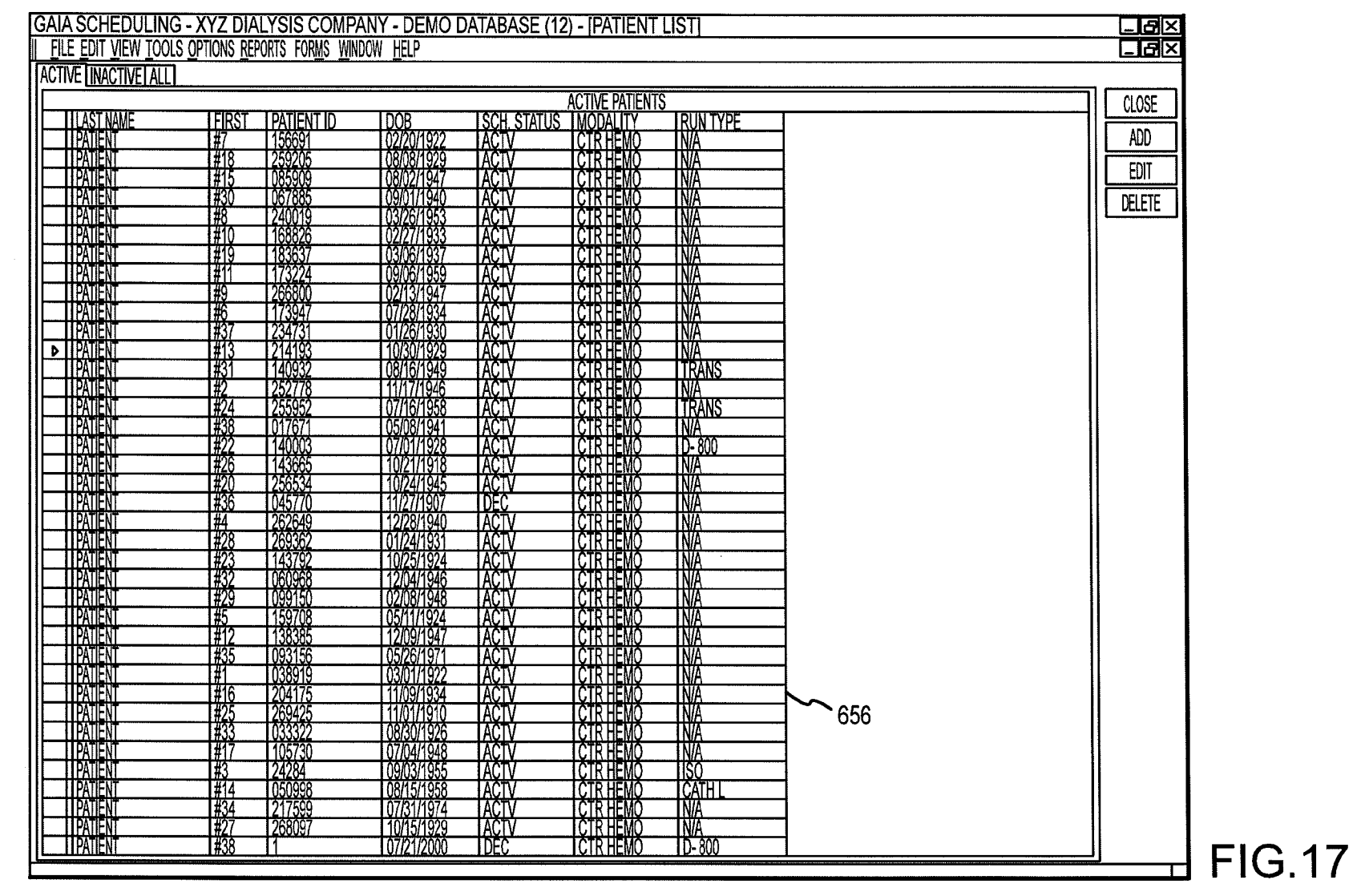

FIG. 16 illustrates a pull-down menu 654 representing various other pop-up windows that may be displayed, such as patient list window 656 (shown in FIG. 17) and employee list window 658 (shown in FIG. 18). As may be appreciated, the list windows 656 and 658 provide access for editing and display of the all the patients in the system and the all the employees in the system, respectively.

Figure 19:
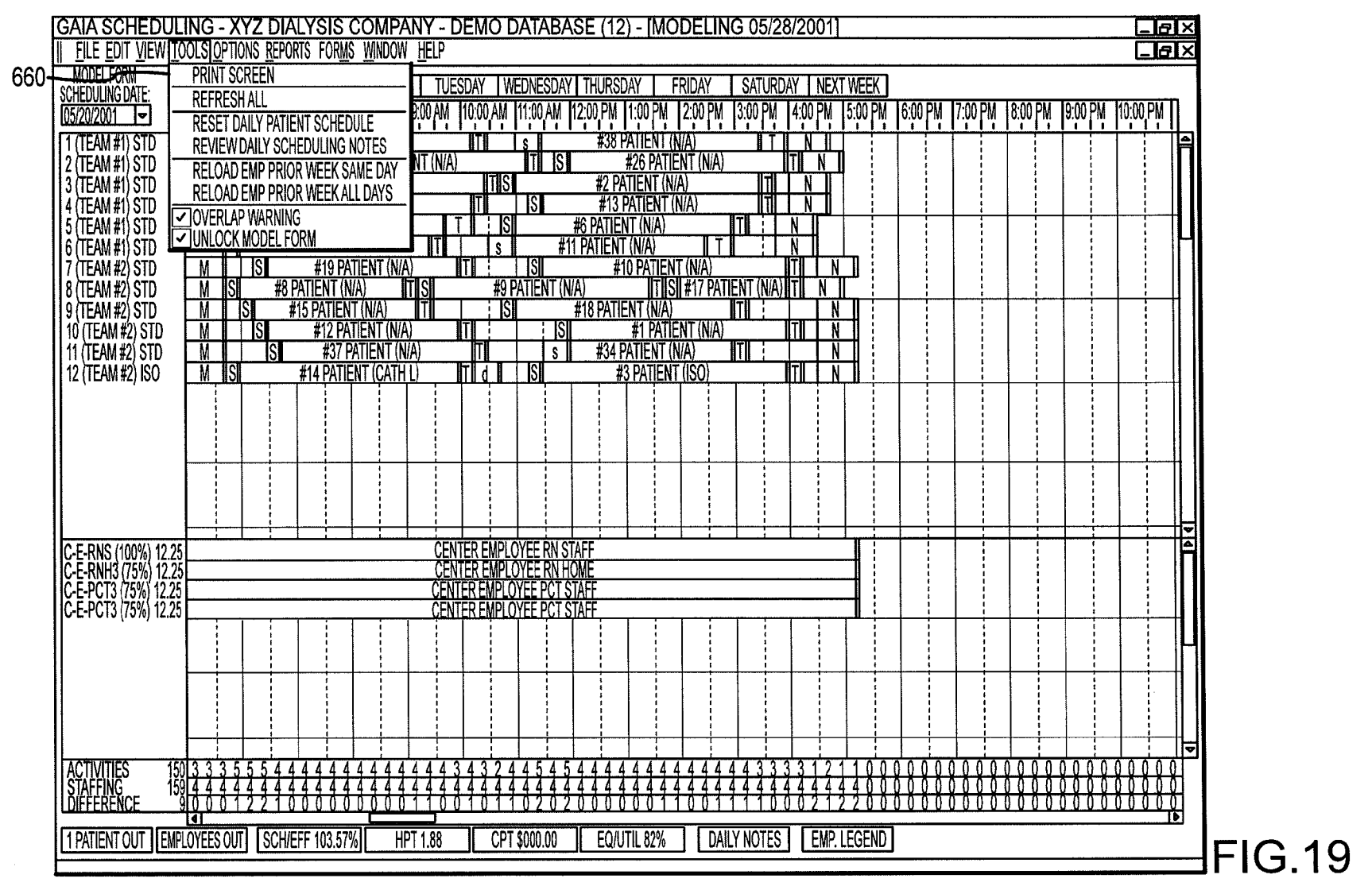
Figure 20:
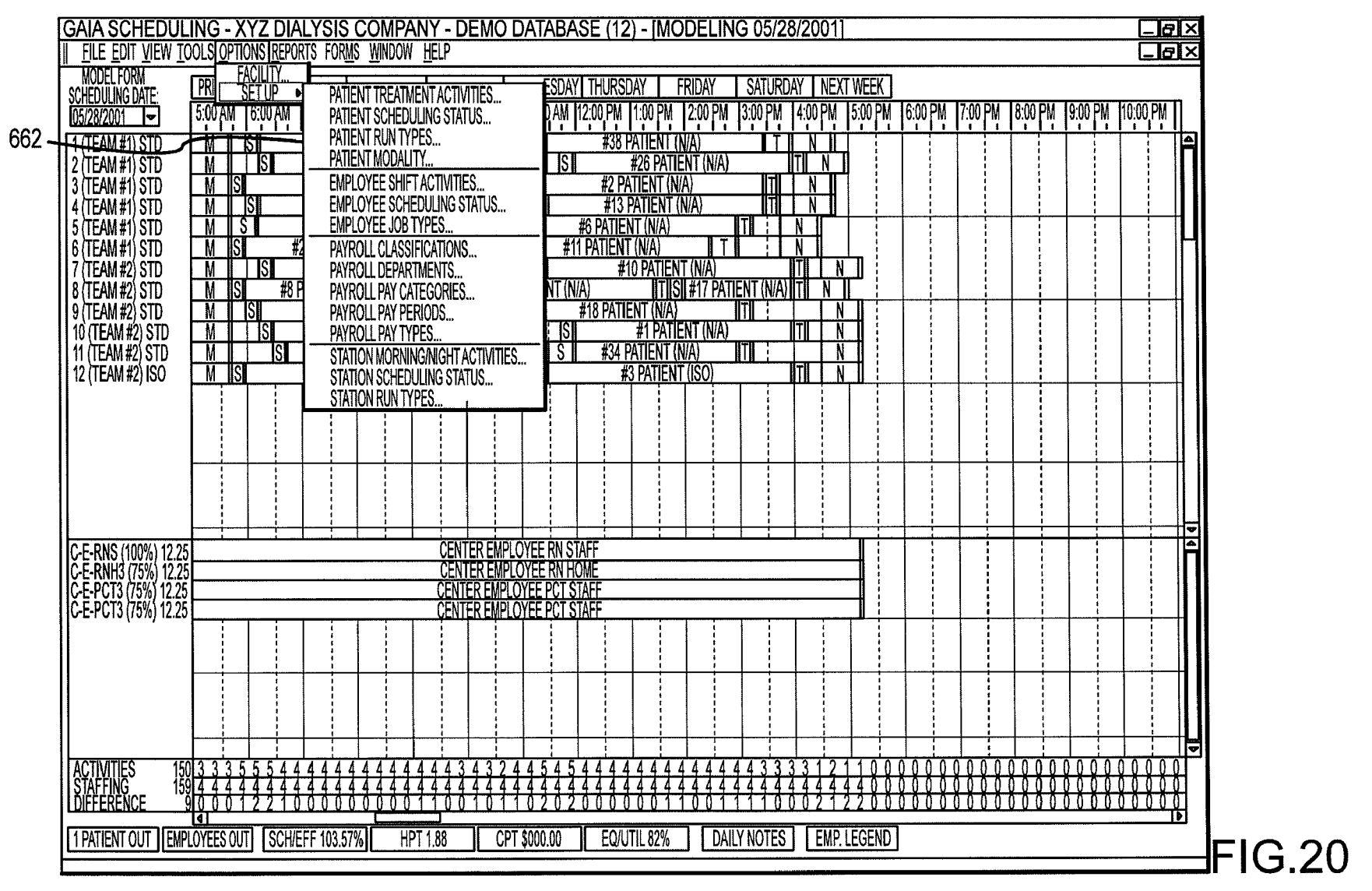
Figure 21:
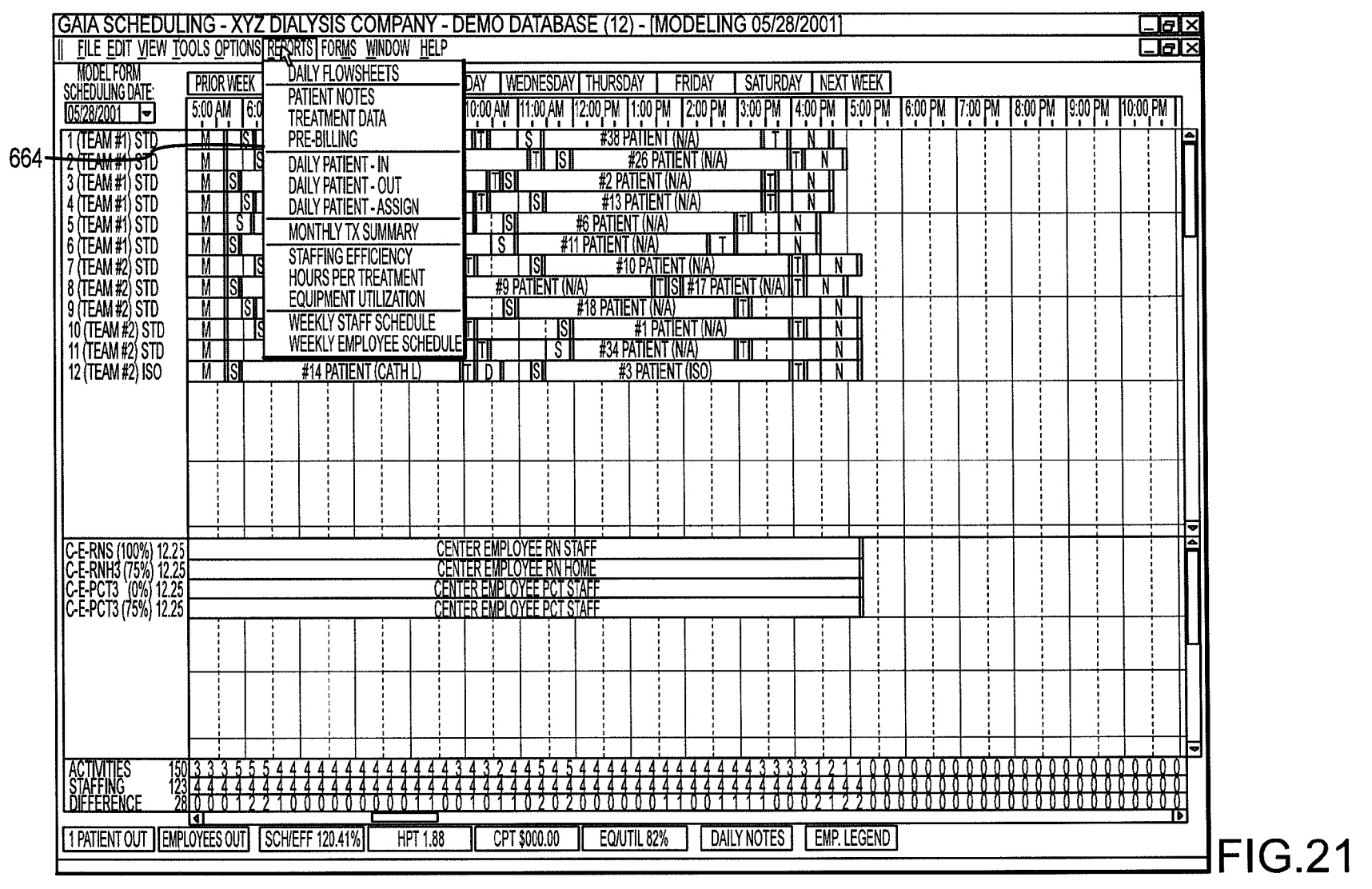
Figure 22:
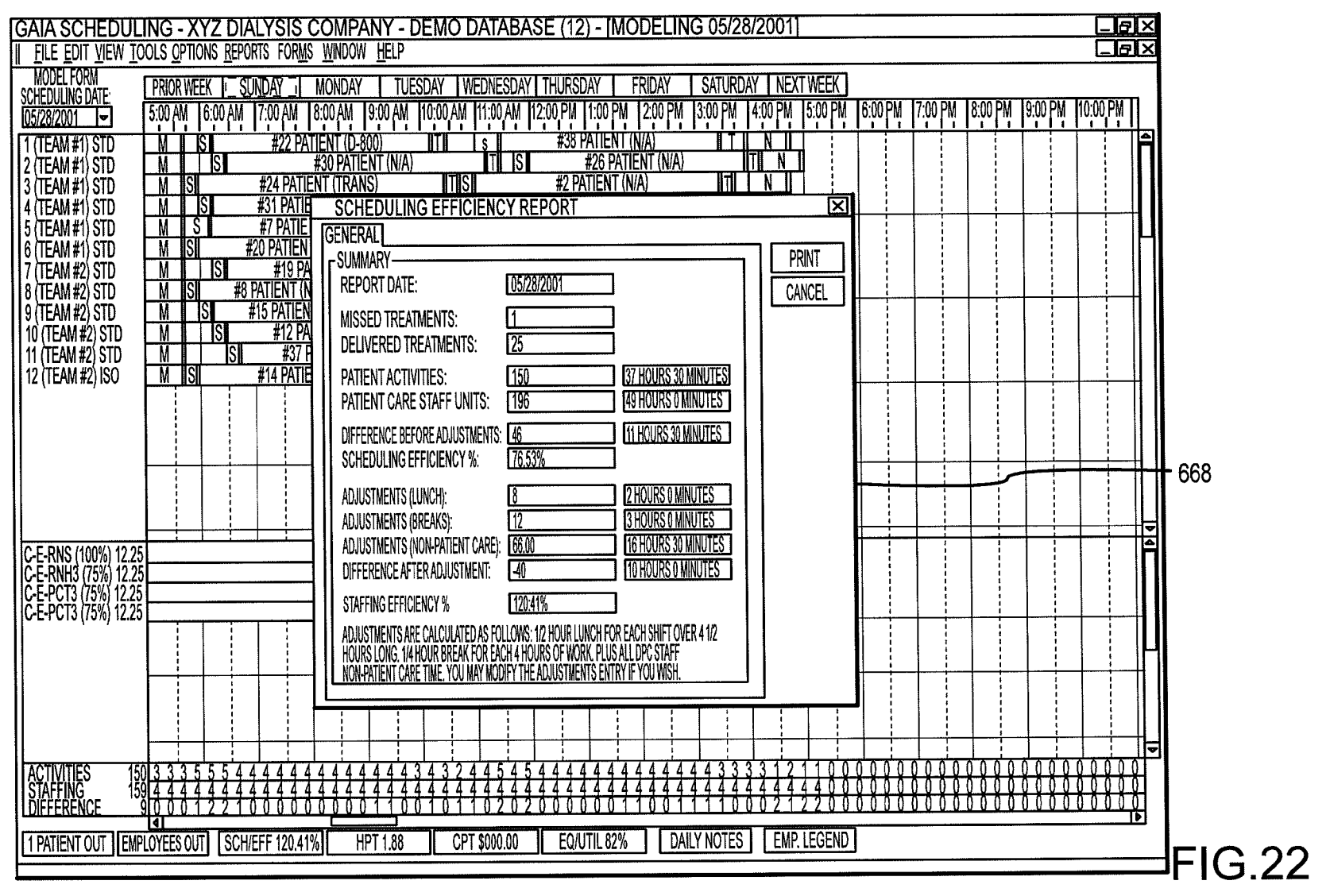

FIGS. 19, 20 and 21 illustrate pull down menus 660, 662 and 664 respectively. Menu 660 relates to various tools or other features that may be used to provide a better user experience. Menu 662, shown in FIG. 20, provides a list of various configuration or setup options that may displayed and configured. Menu 664 provides a list of options relating to various reports that may be generated. One report, the "Scheduling Efficiency Report" 668 is shown in FIG. 21. Another report, the "Hours Per Treatment Report" 670 is shown in FIG. 22.

One such report that may be generated relates to facility utilization. Facility utilization relates to comparing a particular facility's overall capabilities, e.g., total resources operating 100% of the time to meeting patient needs. In other words, the more patients satisfied, the higher the facility utilization. This report may further be used in comparing hours per treatment data to provide efficiency calculations related to the efficiency of the clinic or facility. In another embodiment, other reports relate to staffing efficiency which uses scheduling efficiency but combines other, non-patient care duties into the equation to provide an overall staffing efficiency report. In such a case, the staffing efficiency values can further be used in evaluating the efficiency of a clinic.

The above described system and method provides a significant advantage over prior methods of scheduling employees in the health care industry. In particular, the present system and method provides a means of averaging an employee's time over the course of a shift to more optimally account for the employees tasks and direct patient care availability. For example, if three patients that receive treatments during the same time only require direct patient care one-third of the time, then this system recognizes the fact and only schedules one employee to handle all three patients. Other, prior art methods, would force the scheduling of two or three employees to handle such a situation. Thus, once the empirical data (gathered by the past histories) relating to the needs of each patient has been entered into the system, the system can more efficiently schedule employees. Moreover, adding the empirical data relating to the employees (based on past histories or some other factor), the true capabilities of the employees can be ascertained and thus providing a more efficient scheduling method.

As discussed above, the invention described herein may be implemented as a computer process, a computing system or as an article of manufacture such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

Additionally, although the invention has been described in language specific to structural features and/or methodological steps, it is to be understood that the invention defined in the appended claims is not necessarily limited to the specific features or steps described. Therefore, the specific features and steps are disclosed as preferred forms of implementing the claimed invention.

What is claimed is:

1. A method of scheduling a plurality of patients and a plurality of employees in a health care environment, wherein at least two patients receive treatment during a predetermined time period, said scheduling method comprising:
- for each patient, evaluating patient care requirements, wherein the patient care requirements correspond to actual employee time requirements necessary to satisfy the patient care requirements and evaluating employee time requirements necessary to satisfy non-patient care activities;
- displaying a plurality of patient schedules in relation to time to provide a visual indication of the patient care requirements for each interval;
- in response to the patient care requirement evaluation and the non-patient care requirement evaluation, adjusting scheduling time of at least one patient to distribute the corresponding employee time requirements throughout a predetermined time period, wherein the predetermined time period is a day;
- dividing the day into intervals, wherein each interval is less than an hour;
- in evaluating the patient care requirements, determining the patient care requirements on a per-interval basis;
- scheduling employees in shifts in response to the distributed employee time requirements, wherein scheduling employees in a computer system comprises:
  - (i) determining the employees' patient care capability over intervals of their shift, wherein at least one employee is not capable of performing direct patient care duties for an entire shift;
  - (ii) counting employees at a fractional number based at least upon the employees' training and the predetermined patient care capability resulting in scheduling employees in non-whole number increments; and
  - (iii) rounding up a total amount of employees needed when a determination by a scheduling module results in a fractional number of employees needed to address the needs of the plurality of patients; and
- displaying employee shift information in relation to time to provide a visual indication of scheduled employee information in relation to scheduled patient information.

2. A method as defined in 1 wherein a plurality of job types for an employee are predetermined, each job type having a different patient care capability value associated and wherein the method further comprises:
- scheduling shifts of employees based on job type;
- scheduling employees based on scheduled job type; and
- wherein the patient care capability value is averaged over an entire shift.

3. A method as defined in claim 1 wherein the patient care capability relates to indirect and direct patient care activities.

4. A method as defined in claim 3 wherein each employee further has a predetermined non-patient care capability relating to performing non-patient care activities, and wherein the method further comprises:
- calculating a staff efficiency value based on scheduled activities, wherein the activities relate to patient care and non-patient care activities; and
- displaying the staff efficiency value.

5. A method as defined in claim 1 further comprising:
- calculating a total value of employee time for each interval;
- displaying the calculated employee values; and
- comparing patient requirement values and employee values for each interval to determine efficiency.

6. A method of scheduling a plurality of patients and a plurality of employees as defined in claim 1, further comprising:
- displaying patient schedule information in a patient schedule portion, the patient schedule portion logically divided into intervals and displaying patient schedule information related to the intervals;
- displaying employee schedule information in an employee schedule portion logically divided into intervals, wherein the intervals for the patient schedule portion correspond to the intervals for the employee information portion;
- calculating temporary and permanent patient care requirements and employee capabilities; and
- displaying a calculation display area for displaying calculated values within each interval, the calculated values relating to temporary or permanent patient care requirements and employee capabilities for each interval based on the employee's direct care, indirect care and non-patient care tasks during the time interval, whereby the calculation display area provides efficiency information.

* * * * *